(12) United States Patent
Lofton-Day et al.

(10) Patent No.: US 7,285,394 B2
(45) Date of Patent: Oct. 23, 2007

(54) DISCOVERY AND DIAGNOSTIC METHODS USING 5-METHYLCYTOSINE DNA GLYCOSYLASE

(75) Inventors: Cathy E. Lofton-Day, Brier, WA (US); John K. Day, Renton, WA (US)

(73) Assignee: Epigenomics AG, Berlin (DE)

( * ) Notice: Subject to any disclaimer, the term of this patent is extended or adjusted under 35 U.S.C. 154(b) by 376 days.

(21) Appl. No.: 10/389,853

(22) Filed: Mar. 14, 2003

(65) Prior Publication Data

US 2003/0180779 A1  Sep. 25, 2003

Related U.S. Application Data

(60) Provisional application No. 60/364,689, filed on Mar. 15, 2002.

(51) Int. Cl.
    C12Q 1/34    (2006.01)
    C12Q 1/68    (2006.01)
    C12Q 1/00    (2006.01)

(52) U.S. Cl. ............... 435/18; 435/4; 435/6; 435/15

(58) Field of Classification Search .............. None
    See application file for complete search history.

(56) References Cited

U.S. PATENT DOCUMENTS 6,252,048 B1    6/2001    Kelley et al.
2004/0137456 A1*  7/2004    Yokota et al. ................. 435/6

OTHER PUBLICATIONS

Yan et al. CpG island arrays: an application toward deciphering epigenetic signatures of breast cancer. Clin Cancer Res. Apr. 2000;6(4):1432-8.*
Toyota et al. Identification of differentially methylated sequences in colorectal cancer by methylated CpG island amplification. Cancer Res. May 15, 1999;59(10):2307-12.*
Zhu et al. 5-Methylcytosine DNA glycosylase activity is also present in the human MBD4 (G/T mismatch glycosylase) and in a related avian sequence. Nucleic Acids Res. Nov. 1, 2000;28(21):4157-65.*
Costello et al. Aberrant CpG-island methylation has non-random and tumour-type-specific patterns. Nat Genet. Feb. 2000;25(2):132-8.*
Richards (1997) Cell Mol. Life Sci. 53:790-802.*
Fortini et al., "The Type of DNA Glycosylase Determines the Base Excision Repair Pathway in Mammalian Cells," J. Biol. Chem. 274(21): 15230-15236, 1999.
Ye et al., "Heterogeneous repair of N-Methylpurines at the Nucleotide Level in Normal Human Cells," J. Mol. Biol. 284: 269-285, 1998.

* cited by examiner

*Primary Examiner*—Daniel M. Sullivan
(74) *Attorney, Agent, or Firm*—Barry L. Davison; Davis Wright Tremaine LLP

(57) ABSTRACT

The present invention provides methods for identification of methylated, and/or potentially methylatable CpG dinucleotides in genomic DNA sequences, and methods for isolating genomic DNA sequences comprising methylated CpG dinucleotide sequences. The present invention further provides methods for comparison of the methylation status of specific CpG dinucleotides, and patterns thereof between normal and diseased genomic DNA sequences, along with methods for determining all potentially methylatable CpG dinucleotides in a genomic DNA sample. Specifically, the present invention discloses a novel use of 5-methylcytosine DNA glycosylase (5-MCDG) in combination with art-recognized DNA base excision repair (BER) enzymes, and in particular embodiments, in combination with DNA methyltransferase to specifically label methylated CpG dinucleotide sequences in genomic DNA sequences.

62 Claims, 4 Drawing Sheets

SEQUENCE LISTING

```
<160> NUMBER OF SEQ ID NOS: 13

<210> SEQ ID NO 1
<211> LENGTH: 2470
<212> TYPE: DNA
<213> ORGANISM: Homo sapiens

<400> SEQUENCE: 1
ggcggctgta gccgaggggg cggccggaaa gcagcggcgg cgtctgggc gctttcgcaa      60 cattcagacc tcggttgcag cccggtgccg tgagctgaag aggtttcaca tcttactccg     120
ccccacaccc tgggcgttgc ggcgctgggc tcgttgctgc agccggaccc tgctcgatgg     180
gcacgactgg gctggagagt ctgagtctgg gggaccgcgg agctgccccc accgtcacct     240
ctagtgagcg cctagtccca gacccgccga atgacctccg caaagaagat gttgctatgg     300
aattggaaag agtgggagaa gatgaggaac aaatgatgat aaaaagaagc agtgaatgta     360
atcccttgct acaagaaccc atcgcttctg ctcagtttgg tgctactgca ggaacagaat     420
gccgtaagtc tgtcccatgt ggatgggaaa gagttgtgaa gcaaaggtta tttgggaaga     480
cagcaggaag atttgatgtg tactttatca gcccacaagg actgaagttc agatccaaaa     540
gttcacttgc taattatctt cacaaaaatg gagagacttc tcttaagcca gaagattttg     600
attttactgt actttctaaa aggggtatca agtcaagata taaagactgc agcatggcag     660
ccctgacatc ccatctacaa aaccaaagta acaattcaaa ctggaacctc aggacccgaa     720
gcaagtgcaa aaaggatgtg tttatgccgc caagtagtag ttcagagttg caggagagca     780
gaggactctc taactttact tccactcatt tgcttttgaa agaagatgag ggtgttgatg     840
```

```
atgttaactt cagaaaggtt agaaagccca aaggaaaggt gactattttg aaaggaatcc    900
caattaagaa aactaaaaaa ggatgtagga agagctgttc aggttttgtt caaagtgata    960
gcaaaagaga atctgtgtgt aataaagcag atgctgaaag tgaacctgtt gcacaaaaaa   1020
gtcagcttga tagaactgtc tgcatttctg atgctggagc atgtggtgag accctcagtg   1080
tgaccagtga agaaaacagc cttgtaaaaa aaaagaaag atcattgagt tcaggatcaa    1140
attttgttc tgaacaaaaa acttctggca tcataaacaa attttgttca gccaaagact    1200
cagaacacaa cgagaagtat gaggataccct ttttagaatc tgaagaaatc ggaacaaaag   1260
tagaagttgt ggaaggaaa gaacatttgc atactgacat tttaaaacgt ggctctgaaa    1320
tggacaacaa ctgctcacca accaggaaag acttcactgg tgagaaaata tttcaagaag   1380
ataccatccc acgaacacag atagaaagaa ggaaaacaag cctgtatttt ccagcaaat    1440
ataacaaaga agctcttagc cccccacgac gtaaagcctt taagaaatgg acacctcctc   1500
ggtcaccttt taatctcgtt caagaaacac ttttcatga tccatggaag cttctcatcg    1560
ctactatatt tctcaatcgg acctcaggca aatggcaat acctgtgctt tggaagtttc    1620
tggagaagta tccttcagct gaggtagcaa gaaccgcaga ctggagagat gtgtcagaac   1680
ttcttaaacc tcttggtctc tacgatcttc gggcaaaaac cattgtcaag ttctcagatg   1740
aatacctgac aaagcagtgg aagtatccaa ttgagcttca tgggattggt aaatatggca   1800
acgactctta ccgaattttt tgtgtcaatg agtggaagca ggtgcaccct gaagaccaca   1860
aattaaataa atatcatgac tggctttggg aaaatcatga aaattaagt ctatcttaaa    1920
ctctgcagct ttcaagctca tctgttatgc atagctttgc acttcaaaaa gcttaatta    1980
agtacaacca ccaccttc cagccataga gattttaatt agcccaacta gaagcctagt    2040
gtgtgtgctt tcttaatgtg tgtgccaatg gtggatcttt gctactgaat gtgtttgaac   2100
atgttttgag atttttttaa aataaattat tatttgacaa caatccaaaa aaaatacggc   2160
ttttccaatg atgaaatata atcagaagat gaaaaatagt tttaaactat caataataca   2220
aagcaaattt ctatcagcct tgctaaagct aggggcccac taaatatttt tatcggctag   2280
gcgtggtggt gcatgcctgt aatctcggaa ggctgaggca ggaggatcat ttgagctcat   2340
gagggcccag gaggtcaagg cttcagtgag ccatgatcat gccactgcac tccagtctgg   2400
atgacagaga gagaccctgt ctcaaaaaat atatatttaa aaaataaaaa taaaagctga   2460
ccccaaagac                                                          2470
```

<210> SEQ ID NO 2
<211> LENGTH: 580
<212> TYPE: PRT
<213> ORGANISM: Homo sapiens

<400> SEQUENCE: 2

Met Gly Thr Thr Gly Leu Glu Ser Leu Ser Leu Gly Asp Arg Gly Ala
1               5                   10                  15

Ala Pro Thr Val Thr Ser Ser Glu Arg Leu Val Pro Asp Pro Pro Asn
            20                  25                  30

Asp Leu Arg Lys Glu Asp Val Ala Met Glu Leu Glu Arg Val Gly Glu
        35                  40                  45

Asp Glu Glu Gln Met Met Ile Lys Arg Ser Ser Glu Cys Asn Pro Leu
    50                  55                  60

Leu Gln Glu Pro Ile Ala Ser Ala Gln Phe Gly Ala Thr Ala Gly Thr
65                  70                  75                  80

-continued

```
Glu Cys Arg Lys Ser Val Pro Cys Gly Trp Glu Arg Val Lys Gln
                85                  90                  95
Arg Leu Phe Gly Lys Thr Ala Gly Arg Phe Asp Val Tyr Phe Ile Ser
            100                 105                 110
Pro Gln Gly Leu Lys Phe Arg Ser Lys Ser Ser Leu Ala Asn Tyr Leu
            115                 120                 125
His Lys Asn Gly Glu Thr Ser Leu Lys Pro Asp Phe Asp Phe Thr
        130                 135                 140
Val Leu Ser Lys Arg Gly Ile Lys Ser Arg Tyr Lys Asp Cys Ser Met
145                 150                 155                 160
Ala Ala Leu Thr Ser His Leu Gln Asn Gln Ser Asn Asn Ser Asn Trp
                165                 170                 175
Asn Leu Arg Thr Arg Ser Lys Cys Lys Asp Val Phe Met Pro Pro
            180                 185                 190
Ser Ser Ser Ser Glu Leu Gln Glu Ser Arg Gly Leu Ser Asn Phe Thr
        195                 200                 205
Ser Thr His Leu Leu Leu Lys Glu Asp Glu Gly Val Asp Asp Val Asn
    210                 215                 220
Phe Arg Lys Val Arg Lys Pro Lys Gly Lys Val Thr Ile Leu Lys Gly
225                 230                 235                 240
Ile Pro Ile Lys Lys Thr Lys Lys Gly Cys Arg Lys Ser Cys Ser Gly
                245                 250                 255
Phe Val Gln Ser Asp Ser Lys Arg Glu Ser Val Cys Asn Lys Ala Asp
            260                 265                 270
Ala Glu Ser Glu Pro Val Ala Gln Lys Ser Gln Leu Asp Arg Thr Val
            275                 280                 285
Cys Ile Ser Asp Ala Gly Ala Cys Gly Glu Thr Leu Ser Val Thr Ser
    290                 295                 300
Glu Glu Asn Ser Leu Val Lys Lys Lys Glu Arg Ser Leu Ser Ser Gly
305                 310                 315                 320
Ser Asn Phe Cys Ser Glu Gln Lys Thr Ser Gly Ile Ile Asn Lys Phe
                325                 330                 335
Cys Ser Ala Lys Asp Ser Glu His Asn Glu Lys Tyr Glu Asp Thr Phe
            340                 345                 350
Leu Glu Ser Glu Glu Ile Gly Thr Lys Val Glu Val Val Glu Arg Lys
            355                 360                 365
Glu His Leu His Thr Asp Ile Leu Lys Arg Gly Ser Glu Met Asp Asn
        370                 375                 380
Asn Cys Ser Pro Thr Arg Lys Asp Phe Thr Gly Glu Lys Ile Phe Gln
385                 390                 395                 400
Glu Asp Thr Ile Pro Arg Thr Gln Ile Glu Arg Lys Thr Ser Leu
                405                 410                 415
Tyr Phe Ser Ser Lys Tyr Asn Lys Glu Ala Leu Ser Pro Pro Arg Arg
            420                 425                 430
Lys Ala Phe Lys Lys Trp Thr Pro Pro Arg Ser Pro Phe Asn Leu Val
            435                 440                 445
Gln Glu Thr Leu Phe His Asp Pro Trp Lys Leu Leu Ile Ala Thr Ile
    450                 455                 460
Phe Leu Asn Arg Thr Ser Gly Lys Met Ala Ile Pro Val Leu Trp Lys
465                 470                 475                 480
Phe Leu Glu Lys Tyr Pro Ser Ala Glu Val Ala Arg Thr Ala Asp Trp
                485                 490                 495
```

```
Arg Asp Val Ser Glu Leu Leu Lys Pro Leu Gly Leu Tyr Asp Leu Arg
        500                 505                 510
Ala Lys Thr Ile Val Lys Phe Ser Asp Glu Tyr Leu Thr Lys Gln Trp
        515                 520                 525
Lys Tyr Pro Ile Glu Leu His Gly Ile Gly Lys Tyr Gly Asn Asp Ser
        530                 535                 540
Tyr Arg Ile Phe Cys Val Asn Glu Trp Lys Gln Val His Pro Glu Asp
545                 550                 555                 560
His Lys Leu Asn Lys Tyr His Asp Trp Leu Trp Glu Asn His Glu Lys
                565                 570                 575
Leu Ser Leu Ser
        580

<210> SEQ ID NO 3
<211> LENGTH: 1468
<212> TYPE: DNA
<213> ORGANISM: Gallus gallus

<400> SEQUENCE: 3
gttacggggc gggcggggaa gaggccccgc tgacagcttc ctcttctctc gccccgcagc      60
gctgaaggaa tgaagctgcg gtcccaacgg gcgctcacgg agcggtgccg tcccgccggg     120
cgggcagcgg gaggcggtgc cggtgggacc gcaggcagcg atgggagccg cgctgcgccg     180
cgggacctcc ccgtgcggga cggcggagag ggcggagcgc ggagctccca gcagcgccat     240
gggaccgctg tgcgctgcga gcgtccgagc gcgaggggcg gaaaagccga gcggtgcgcg     300
accaaagcag aggcgggcgg gagagcgagg aggagctccg cgagaagcga tgcagggagc     360
gagcggggga gagcggag agcggcgcgt ggcgaccggg aagcggcggg cgttcaaaac       420
gaggcgccgt gtgaggaggc ggcgcgtgtc cgtcacggcc aggcggtggc tgagctgcgc     480
gcaccgcccg cggctgccgg cacgcagtgc gtccctgccg ggcagcgccc ggagccgcag     540
ccgggagcgg ccgcagaccg cctgcagggg cggccgcaga gcgcggcggg tggaggtgag     600
cggacgggcg ctgggacggc acctgctgtg ctcggcgagg aggaaagcag cgggtggaag     660
acgggggaag agaccgagcc gggggatccg ggtacgcggg actccgcagc tgatggcgat     720
gtctcgtggc cttctgacaa gaaaagcttc acagcagttc aagcgccacg aggtacagaa     780
gaatctgccc cacggacaca ggtggacagg aggaaaacga gtccatattt ttcaagtaaa     840
tacagcaaag aagctctcag cccacccagg aggaaggcct tcagaaagtg gactcctcca     900
cgctcccccct tcaatttggt acaagaaaca cttttccatg atccatggaa acttctcatt     960
gcgaccatat ttctcaataa gacctcaggt aaaatggcaa ttcctgtgct ctgggagttc    1020
ctcaggaagt acccctctcc cgaagtagcc agaactgcag actggaagga gatgtcggag    1080
ctgctcagac ctctcggcct ttatgcactc agagcaaaaa ctataatcaa gttttcagac    1140
gagtacctga acaagcagtg gaagtacccc attgagctgc acggaatcgg aaagtacgga    1200
aatgactcct acagaatctt ctgcgtcaat gaatggaaag aggtacagcc acaggaccac    1260
aagttgaaca tctaccacgc gtggctctgg gagaaccatg agaagctgag cgtggactga    1320
gtgcagccgc catgcgtgcc aacggtgagc tgtgcagcct cagccctgtg ctgaacatca    1380
cgttcttagt ttatatgttg gtgtgacatt ggactcagat aatcgctgta ataaaacgtt    1440
caaatgctta aaaaaaaaaa aaaaaaa                                        1468

<210> SEQ ID NO 4
<211> LENGTH: 416
```

```
<212> TYPE: PRT
<213> ORGANISM: Gallus gallus

<400> SEQUENCE: 4

Met Lys Leu Arg Ser Gln Arg Ala Leu Thr Glu Arg Cys Arg Pro Ala
1               5                   10                  15

Gly Arg Ala Ala Gly Gly Ala Gly Gly Thr Ala Ala Pro Asp Gly
            20                  25                  30

Ser Arg Ala Ala Pro Arg Asp Leu Pro Val Arg Asp Gly Gly Gly
        35                  40                  45

Gly Ala Arg Ser Ser Gln Gln Arg His Gly Thr Ala Val Arg Cys Glu
    50                  55                  60

Arg Pro Ser Ala Arg Gly Gly Lys Ala Glu Arg Cys Ala Thr Lys Ala
65                  70                  75                  80

Glu Ala Gly Gly Arg Ala Arg Arg Ser Ser Ala Arg Ser Asp Ala Gly
                85                  90                  95

Ser Glu Arg Gly Lys Arg Arg Ala Ala Arg Gly Asp Arg Glu Ala
            100                 105                 110

Ala Gly Val Gln Asn Glu Ala Pro Cys Glu Glu Ala Ala Arg Val Arg
        115                 120                 125

His Gly Gln Ala Val Ala Glu Leu Arg Ala Pro Pro Ala Ala Gly
    130                 135                 140

Thr Gln Cys Val Pro Ala Gly Gln Arg Pro Glu Pro Gln Pro Gly Ala
145                 150                 155                 160

Ala Ala Asp Arg Leu Gln Gly Arg Pro Gln Ser Ala Ala Gly Gly Gly
                165                 170                 175

Glu Arg Thr Gly Ala Gly Thr Ala Pro Ala Val Leu Gly Glu Glu Glu
            180                 185                 190

Ser Ser Gly Trp Lys Thr Gly Glu Glu Thr Glu Pro Gly Asp Pro Gly
        195                 200                 205

Thr Arg Asp Ser Ala Ala Asp Gly Asp Val Ser Trp Pro Ser Asp Lys
        210                 215                 220

Lys Ser Phe Thr Ala Val Gln Ala Pro Arg Gly Thr Glu Glu Ser Ala
225                 230                 235                 240

Pro Arg Thr Gln Val Asp Arg Arg Lys Thr Ser Pro Tyr Phe Ser Ser
                245                 250                 255

Lys Tyr Ser Lys Glu Ala Leu Ser Pro Pro Arg Arg Lys Ala Phe Arg
            260                 265                 270

Lys Trp Thr Pro Pro Arg Ser Pro Phe Asn Leu Val Gln Glu Thr Leu
        275                 280                 285

Phe His Asp Pro Trp Lys Leu Leu Ile Ala Thr Ile Phe Leu Asn Lys
        290                 295                 300

Thr Ser Gly Lys Met Ala Ile Pro Val Leu Trp Glu Phe Leu Arg Lys
305                 310                 315                 320

Tyr Pro Ser Pro Glu Val Ala Arg Thr Ala Asp Trp Lys Glu Met Ser
                325                 330                 335

Glu Leu Leu Arg Pro Leu Gly Leu Tyr Ala Leu Arg Ala Lys Thr Ile
            340                 345                 350

Ile Lys Phe Ser Asp Glu Tyr Leu Asn Lys Gln Trp Lys Tyr Pro Ile
        355                 360                 365

Glu Leu His Gly Ile Gly Lys Tyr Gly Asn Asp Ser Tyr Arg Ile Phe
        370                 375                 380

Cys Val Asn Glu Trp Lys Glu Val Gln Pro Gln Asp His Lys Leu Asn
385                 390                 395                 400
```

Ile Tyr His Ala Trp Leu Trp Glu Asn His Glu Lys Leu Ser Val Asp
            405                 410                 415

<210> SEQ ID NO 5
<211> LENGTH: 3410
<212> TYPE: DNA
<213> ORGANISM: Homo sapiens

<400> SEQUENCE: 5

| | | | | | | |
|---|---|---|---|---|---|---|
| gcaccaggcg | cccagtggag | ccgtttggga | gaattgcctg | cgccacgcag | cggggccgga | 60 |
| caggcggtaa | ggatctgatt | aggctttcga | acttgagttt | gactgatgtc | ttctgtgtgg | 120 |
| tgtccgctaa | atcccacagc | ataggatc | agtcgcattg | gttataaggt | ttgcttctgg | 180 |
| ctgggtgcgg | tggctcatgc | ctgtaatcca | acattgggag | gccaaggcag | gcggaccacc | 240 |
| tgaagtcggg | agcttgagtc | cagccactgt | ctgggtactg | ccagccatcg | ggcccaggtc | 300 |
| tctggggttg | tcttaccgca | gtgagtacca | cgcggtacta | cagagaccgg | ctgcccgtgt | 360 |
| gcccggcagg | tggagccgcc | gcatcagcgg | cctcgggaa | tggaagcgga | gaacgcgggc | 420 |
| agctattccc | ttcagcaagc | tcaagctttt | tatacgtttc | catttcaaca | actgatggct | 480 |
| gaagctccta | atatggcagt | tgtgaatgaa | cagcaaatgc | cagaagaagt | tccagcccca | 540 |
| gctcctgctc | aggaaccagt | gcaagaggct | ccaaaaggaa | gaaaagaaa | acccagaaca | 600 |
| acagaaccaa | acaaccagt | ggaacccaaa | aaacctgttg | agtcaaaaaa | atctggcaag | 660 |
| tctgcaaaac | caaagaaaa | acaagaaaaa | attacagaca | catttaaagt | aaaaagaaaa | 720 |
| gtagaccgtt | ttaatggtgt | tcagaagct | gaacttctga | ccaagactct | ccccgatatt | 780 |
| ttgaccttca | atctggacat | tgtcattatt | ggcataaacc | cgggactaat | ggctgcttac | 840 |
| aaagggcatc | attaccctgg | acctggaaac | cattttggga | agtgtttgtt | tatgtcaggg | 900 |
| ctcagtgagg | tccagctgaa | ccatatggat | gatcacactc | taccagggaa | gtatggtatt | 960 |
| ggatttacca | acatggtgga | aaggaccacg | cccggcagca | aagatctctc | cagtaaagaa | 1020 |
| tttcgtgaag | gaggacgtat | tctagtacag | aaattacaga | aatatcagcc | acgaatagca | 1080 |
| gtgtttaatg | gaaatgtat | ttatgaaatt | tttagtaaag | aagttttttgg | agtaaaggtt | 1140 |
| aagaacttgg | aatttgggct | tcagccccat | aagattccag | acacagaaac | tctctgctat | 1200 |
| gttatgccat | catccagtgc | aagatgtgct | cagtttcctc | gagcccaaga | caaagttcat | 1260 |
| tactacataa | aactgaagga | cttaagagat | cagttgaaag | gcattgaacg | aaatatggac | 1320 |
| gttcaagagg | tgcaatatac | atttgaccta | cagcttgccc | aagaggatgc | aaagaagatg | 1380 |
| gctgttaagg | aagaaaaata | tgatccaggt | tatgaggcag | catatggtgg | tgcttacgga | 1440 |
| gaaaatccat | gcagcagtga | accttgtggc | ttctcttcaa | atgggctaat | tgagagcgtg | 1500 |
| gagttaagag | gagaatcagc | tttcagtggc | attcctaatg | gcagtggat | gacccagtca | 1560 |
| tttacagacc | aaattccttc | ctttagtaat | cactgtggaa | cacaagaaca | ggaagaagaa | 1620 |
| agccatgctt | aagaatggtg | cttctcagct | ctgcttaaat | gctgcagttt | taatgcagtt | 1680 |
| gtcaacaagt | agaacctcag | tttgctaact | gaagtgtttt | attagtattt | tactctagtg | 1740 |
| gtgtaattgt | aatgtagaac | agttgtgtgg | tagtgtgaac | cgtatgaacc | taagtagttt | 1800 |
| ggaagaaaaa | gtagggtttt | tgtatactag | cttttgtatt | tgaattaatt | atcattccag | 1860 |
| cttttttatat | actatatttc | atttatgaag | aaattgattt | tcttttggga | gtcacttttca | 1920 |
| atctgtaatt | ttaaaataca | agtctgaata | tttatagttg | attcttaact | gtgcataaac | 1980 |
| ctagatatac | cattatccct | tttataccta | agaagggcat | gctaataatt | accactgtca | 2040 |

```
aagaggcaaa ggtgttgatt tttgtatata agttaagcct cagtggagtc tcatttgtta    2100 gttttttagtg gtaactaagg gtaaactcag ggttccctga gctatatgca cactcagacc    2160
tctttgcttt accagtggtg tttgtgagtt gctcagtagt aaaaactggc ccttacctga    2220
cagagccctg gctttgacct gctcagccct gtgtgttaat cctctagtag ccaattaact    2280
actctggggt ggcaggttcc agagaatcga gtagaccttt tgccactcat ctgtgtttta    2340
cttgagacat gtaaatatga tagggaagga actgaatttc tccattcata tttataacca    2400 ttctagttttt atcttccttg gctttaagag tgtgccatgg aaagtgataa gaaatgaact    2460
tctaggctaa gcaaaaagat gctggagata tttgatactc tcatttaaac tggtgcttta    2520
tgtacatgag atgtactaaa ataagtaata tagaattttt cttgctaggt aaatccagta    2580
agccaataat tttaaagatt ctttatctgc atcattgctg tttgttacta taaattaaat    2640
gaacctcatg gaaaggttga ggtgtatacc tttgtgattt tctaatgagt tttccatggt    2700
gctacaaata atccagacta ccaggtctgg tagatattaa agctgggtac taagaaatgt    2760
tatttgcatc ctctcagtta ctcctgaata ttctgatttc atacgtaccc agggagcatg    2820
ctgttttgtc aatcaatata aaatatttat gaggtctccc ccaccccccag gaggttatat    2880 gattgctctt ctctttataa taagagaaac aaattcttat tgtgaatctt aacatgcttt    2940
ttagctgtgg ctatgatgga ttttattttt tcctaggtca agctgtgtaa aagtcattta    3000
tgttatttaa atgatgtact gtactgctgt ttacatggac gttttgtgcg ggtgctttga    3060
agtgccttgc atcagggatt aggagcaatt aaattatttt ttcacgggac tgtgtaaagc    3120
atgtaactag gtattgcttt ggtatataac tattgtagct ttacaagaga ttgttttatt    3180
tgaatgggga aaatacccctt taattatga cggacatcca ctagagatgg gtttgaggat    3240
tttccaagcg tgtaataatg atgtttttcc taacatgaca gatgagtagt aaatgttgat    3300
atatcctata catgacagtg tgagactttt tcattaaata atattgaaag attttaaaat    3360
tcatttgaaa gtctgatggc ttttacaata aaagatatta agaattgtta              3410
```

<210> SEQ ID NO 6
<211> LENGTH: 410
<212> TYPE: PRT
<213> ORGANISM: Homo sapiens

<400> SEQUENCE: 6

```
Met Glu Ala Glu Asn Ala Gly Ser Tyr Ser Leu Gln Gln Ala Gln Ala
1               5                   10                  15

Phe Tyr Thr Phe Pro Phe Gln Gln Leu Met Ala Glu Ala Pro Asn Met
            20                  25                  30

Ala Val Val Asn Glu Gln Gln Met Pro Glu Glu Val Pro Ala Pro Ala
        35                  40                  45

Pro Ala Gln Glu Pro Val Gln Glu Ala Pro Lys Gly Arg Lys Arg Lys
    50                  55                  60

Pro Arg Thr Thr Glu Pro Lys Gln Pro Val Glu Pro Lys Lys Pro Val
65                  70                  75                  80

Glu Ser Lys Lys Ser Gly Lys Ser Ala Lys Pro Lys Glu Lys Gln Glu
                85                  90                  95

Lys Ile Thr Asp Thr Phe Lys Val Lys Arg Lys Val Asp Arg Phe Asn
            100                 105                 110

Gly Val Ser Glu Ala Glu Leu Leu Thr Lys Thr Leu Pro Asp Ile Leu
        115                 120                 125
```

| Thr | Phe | Asn | Leu | Asp | Ile | Val | Ile | Ile | Gly | Ile | Asn | Pro | Gly | Leu | Met |
|-----|-----|-----|-----|-----|-----|-----|-----|-----|-----|-----|-----|-----|-----|-----|-----|
| | | | 130 | | | | 135 | | | | 140 | | | | |

Ala Ala Tyr Lys Gly His His Tyr Pro Gly Pro Gly Asn His Phe Trp
145                    150                      155                     160

Lys Cys Leu Phe Met Ser Gly Leu Ser Glu Val Gln Leu Asn His Met
                  165                    170                    175

Asp Asp His Thr Leu Pro Gly Lys Tyr Gly Ile Gly Phe Thr Asn Met
              180                    185                    190

Val Glu Arg Thr Thr Pro Gly Ser Lys Asp Leu Ser Ser Lys Glu Phe
          195                  200                  205

Arg Glu Gly Gly Arg Ile Leu Val Gln Lys Leu Gln Lys Tyr Gln Pro
210                    215                      220

Arg Ile Ala Val Phe Asn Gly Lys Cys Ile Tyr Glu Ile Phe Ser Lys
225                    230                    235                    240

Glu Val Phe Gly Val Lys Val Lys Asn Leu Glu Phe Gly Leu Gln Pro
              245                    250                    255

His Lys Ile Pro Asp Thr Glu Thr Leu Cys Tyr Val Met Pro Ser Ser
          260                  265                  270

Ser Ala Arg Cys Ala Gln Phe Pro Arg Ala Gln Asp Lys Val His Tyr
        275                  280                  285

Tyr Ile Lys Leu Lys Asp Leu Arg Asp Gln Leu Lys Gly Ile Glu Arg
290                    295                    300

Asn Met Asp Val Gln Glu Val Gln Tyr Thr Phe Asp Leu Gln Leu Ala
305                    310                    315                  320

Gln Glu Asp Ala Lys Lys Met Ala Val Lys Glu Lys Tyr Asp Pro
              325                    330                  335

Gly Tyr Glu Ala Ala Tyr Gly Gly Ala Tyr Gly Glu Asn Pro Cys Ser
            340                  345                  350

Ser Glu Pro Cys Gly Phe Ser Ser Asn Gly Leu Ile Glu Ser Val Glu
          355                360                  365

Leu Arg Gly Glu Ser Ala Phe Ser Gly Ile Pro Asn Gly Gln Trp Met
370                    375                    380

Thr Gln Ser Phe Thr Asp Gln Ile Pro Ser Phe Ser Asn His Cys Gly
385                    390                    395                  400

Thr Gln Glu Gln Glu Glu Ser His Ala
          405                  410

<210> SEQ ID NO 7
<211> LENGTH: 3233
<212> TYPE: DNA
<213> ORGANISM: Gallus gallus

<400> SEQUENCE: 7

```
gcggggtgcc gcgctcggcc atggaggccg aggagctggg caggtattac gcttatctcc      60
agcaagctca agctttttac acgtttccgt tccaccagat gatgactgca ccgcctacca     120
tggaagccat gactgagcag ccgactctag agggcattcc agagccaaac cttgctcagg     180
aacctcctaa agaagttaaa aagggtggaa ggaagagaaa agccaaagca actgagccaa     240
agcaacccaa aaagcctgct gctaagaaag aaaaagcgac caagtcgaaa gggaaacaag     300
aaagattacg gacactttt aaagtgaaaa gaaagtggaa ccgttttaat ggtgtgtctg     360
aagctgagct gctgacaaag actttacctg atattttgac cttcgatctg gacatcgtaa     420
taattggcat aaacccggc ttgatggcag cttacaaagg gcatcattac cctggacctg     480
gaaaccattt ttggaagtgt ctcttcatgt ctggtctaag taatgaacag ctgaaccata     540
```

```
tggatgacca caccttaccg cataaatacg ggattggatt tacaaatatg gtggaaagga      600
caacacctgg aagcaaagac ctctccagta aagagtttcg agaaggaggg cgaattctga      660
tgcagaaatt acagaagtat aaacctcgta tagcagcttt caatgaaaaa tgtatctatg      720
aaattttag tagagaagta tttggaataa gagttaagaa cttggaattt ggattgcagc       780
cccacaaggt accagagaca gaaactctgt gctacgttat gccatcatcc agtgcaagat      840
gtgctcagtt ccctcgtgcg caagataaag ttcattatta cataaagcta aaagacttaa      900
gggatcagct gaaaggcatt gcaccaaaca cagaggtgca ggaagtgcag tacacatttg      960
acttacagct tgcacaagag gatgctaaaa agatggctgt caaggaagaa aagtacgatc     1020
caggttatga agcagcatat ggaggagctt actgcgatcg tgcgccatat gaaagcgaac     1080
agtgcaattt ctcttcaaat ggaactgcac caagcaatcc ccagtactgt gagggtcat     1140
cttttggtga agttcctaat ggacaatgga tgacgcagtc ctttgcagac cagattccag     1200
aattcagtgc tggtatgaca caagaacgag agggaagcag tgcataagag ctctttcttc     1260
tcagctacgc atacatgctg cagttttaat gcagtgatca agattggtac ctcggttctc     1320
caactgaagc attttaatag tattttatct cccttagata ttttattata gtcctaaata     1380
agtgtgtggt aggctccaat caatgaacta ggtaatttta aggaactgtc caaacttgaa     1440
aaaaaaaga agttagccct ttttttgtat atgagttta tatttaatgt ctgccatttc       1500
ttgcagtttt tgacaaactg cttttccatc tgtgaaggtt ctttagggt gttaatttta      1560
ttccataaat tgtaaagtag gagtaagagc agcagtatac ttttattga cgcatcgata     1620
tttggatatc tcatagtgct tttatatcta gaggggaaaa tggaagtgta cccttatctt     1680
acacaaagtg gtgttttaa tcatgcacag ttaaacaaat ggtgcttttt aagactccct     1740
ttgcacttca gggcaggaat agagagctct gtctatttgg tgactggacc atagtcaggt     1800
ttaagggagc agagacaact catcactggt caggaaaatc ggcgtcacac aggacagggc     1860
ctaaatatt ctagtcttag aataaagtgt tcttatcatt ccgtctcttt ctcccttaaa     1920
ttctagtgta aggaactgga attccttaaa aagaaaagt ggttctcaaa tctgtggcgt      1980
ttgtcagtca cttctttgtg attagtctct tctcctgaac cttagcaagt gaacagttta     2040
tatggcaggg aactgaaaga ctgtattccc tgtaagaacc catctgcagt tatgttgttt     2100
gtgtcaggta cagctagcac agggtgaaag aagatggtgc tttagcagtt ttttgtatta     2160
attctcttc aagaccttag agggtgtttt tcttacccat cttatgtgta aaaaaaatta      2220
ctaagttgaa gacaagggca gctgttccat gaattaagtt gacagctgtt ggaactacag     2280
cttcttctg aggaacttgc tccaacaata cacaattgca gccaatgttg gcgactgaga      2340
aagaaggag attctatgct tgtgcctaac catcatctac tttccctctt ctatcacgtg     2400
aggaggagac gaagtaaaag caataagctg atcaaaacgt tcacgttttg atgatcttat     2460
gagagaaggt gcttcacata cttgaaaaat agatccaagc agtatctcca cacacggtgc     2520
tggtcagagg ttcctgttcg gtgctttatc ctttcctcac agccgctgac ggctgccatg     2580
cactgagtgc aattagttgg cgtggatact aatcctgctg taacagctcg cactgagctc     2640
acacactgcc atcctgttgt gaggcaggca tgatgtttac agtcctcttt ccaaattatg     2700
tggcttaatt ctgagcgtct gaaatcaaga aagcgtgcat tatgattgtg tttatcagct     2760
tcagcataaa gctgctccgt atgttgtcag aacggcatag gatttgtctt gtctgttatt     2820
taagtgtac tgtatcacgt attgctgttt acatggacgt tttcccacag gtgctccaag      2880
```

-continued

```
tacctcacat caggggatttg ttacaattca gttttatttt tcagcaagat tagaagcatg    2940
taacttagca ctgctggtga ggtggcacag tagtacagaa ctactgtact gctctcctgt    3000
tggagttgaa gggaaaggtc tcttctggaa cagaggcacc tactaggtat aaaatacagt    3060
tgtgtgtata atgaccgttt cactcagtac tgcagtttgt ggtactccct cgggaccggt    3120
gctcttttca ttacagtaat ccagaggttc ttaatctgtc ttaaatctct ctctgtttca    3180
caataaaatc aggaattgta aaaaaaaaaa aaaaaaaaa aaaaaaaaaa aaa            3233
```

<210> SEQ ID NO 8
<211> LENGTH: 408
<212> TYPE: PRT
<213> ORGANISM: Gallus gallus

<400> SEQUENCE: 8

```
Met Glu Ala Glu Leu Gly Arg Tyr Tyr Ala Tyr Leu Gln Gln Ala
1               5                   10                  15

Gln Ala Phe Tyr Thr Phe Pro Phe His Gln Met Met Thr Ala Pro Pro
            20                  25                  30

Thr Met Glu Ala Met Thr Glu Gln Pro Thr Leu Glu Gly Ile Pro Glu
        35                  40                  45

Pro Asn Leu Ala Gln Glu Pro Pro Lys Glu Val Lys Lys Gly Gly Arg
    50                  55                  60

Lys Arg Lys Ala Lys Ala Thr Glu Pro Lys Gln Pro Lys Lys Pro Ala
65                  70                  75                  80

Ala Lys Lys Glu Lys Ala Thr Lys Ser Lys Gly Lys Gln Glu Lys Ile
                85                  90                  95

Thr Asp Thr Phe Lys Val Lys Arg Lys Val Asp Arg Phe Asn Gly Val
            100                 105                 110

Ser Glu Ala Glu Leu Leu Thr Lys Thr Leu Pro Asp Ile Leu Thr Phe
        115                 120                 125

Asp Leu Asp Ile Val Ile Ile Gly Ile Asn Pro Gly Leu Met Ala Ala
    130                 135                 140

Tyr Lys Gly His His Tyr Pro Gly Pro Gly Asn His Phe Trp Lys Cys
145                 150                 155                 160

Leu Phe Met Ser Gly Leu Ser Asn Glu Gln Leu Asn His Met Asp Asp
                165                 170                 175

His Thr Leu Pro His Lys Tyr Gly Ile Gly Phe Thr Asn Met Val Glu
            180                 185                 190

Arg Thr Thr Pro Gly Ser Lys Asp Leu Ser Ser Lys Glu Phe Arg Glu
        195                 200                 205

Gly Gly Arg Ile Leu Met Gln Lys Leu Gln Lys Tyr Lys Pro Arg Ile
    210                 215                 220

Ala Ala Phe Asn Gly Lys Cys Ile Tyr Glu Ile Phe Ser Arg Glu Val
225                 230                 235                 240

Phe Gly Ile Arg Val Lys Asn Leu Glu Phe Gly Leu Gln Pro His Lys
                245                 250                 255

Val Pro Glu Thr Glu Thr Leu Cys Tyr Val Met Pro Ser Ser Ser Ala
            260                 265                 270

Arg Cys Ala Gln Phe Pro Arg Ala Gln Asp Lys Val His Tyr Tyr Ile
        275                 280                 285

Lys Leu Lys Asp Leu Arg Asp Gln Leu Lys Gly Ile Ala Pro Asn Thr
    290                 295                 300

Glu Val Gln Glu Val Gln Tyr Thr Phe Asp Leu Gln Leu Ala Gln Glu
305                 310                 315                 320
```

```
Asp Ala Lys Lys Met Ala Val Lys Glu Glu Lys Tyr Asp Pro Gly Tyr
            325                 330                 335

Glu Ala Ala Tyr Gly Gly Ala Tyr Cys Asp Arg Ala Pro Tyr Glu Ser
            340                 345                 350

Glu Gln Cys Asn Phe Ser Ser Asn Gly Thr Ala Pro Ser Asn Pro Gln
            355                 360                 365

Tyr Cys Glu Gly Ser Ser Phe Gly Val Pro Asn Gly Gln Trp Met
    370                 375                 380

Thr Gln Ser Phe Ala Asp Gln Ile Pro Glu Phe Ser Ala Gly Met Thr
385                 390                 395                 400

Gln Glu Arg Glu Gly Ser Ser Ala
            405
```

<210> SEQ ID NO 9
<211> LENGTH: 3410
<212> TYPE: DNA
<213> ORGANISM: Homo sapiens
<220> FEATURE:
<221> NAME/KEY: variation
<222> LOCATION: (670)..(670)
<223> OTHER INFORMATION: Applicants herein disclose a C to T variant at
      this nucleotide position

<400> SEQUENCE: 9

```
gcaccaggcg cccagtggag ccgtttggga gaattgcctg cgccacgcag cggggccgga    60
caggcggtaa ggatctgatt aggctttcga acttgagttt gactgatgtc ttctgtgtgg   120
tgtccgctaa atcccacagc ataggatc agtcgcattg gttataaggt ttgcttctgg   180
ctgggtgcgg tggctcatgc ctgtaatcca acattgggag gccaaggcag gcggaccacc   240
tgaagtcggg agcttgagtc cagccactgt ctgggtactg ccagccatcg ggcccaggtc   300
tctggggttg tcttaccgca gtgagtacca cgcggtacta cagagaccgg ctgcccgtgt   360
gcccggcagg tggagccgcc gcatcagcgg cctcgggaa tggaagcgga gaacgcgggc   420
agctattccc ttcagcaagc tcaagctttt tatacgtttc catttcaaca actgatggct   480
gaagctccta atatggcagt tgtgaatgaa cagcaaatgc cagaagaagt tccagcccca   540
gctcctgctc aggaaccagt gcaagaggct ccaaaaggaa gaaaaagaaa acccagaaca   600
acagaaccaa acaaccagt ggaacccaaa aaacctgttg agtcaaaaaa atctggcaag   660
tctgcaaaat caaagaaaa acaagaaaaa attacagaca catttaaagt aaaaagaaaa   720
gtagaccgtt ttaatggtgt ttcagaagct gaacttctga ccaagactct ccccgatatt   780
ttgaccttca atctggacat tgtcattatt ggcataaacc cgggactaat ggctgcttac   840
aaagggcatc attaccctgg acctggaaac cattttttgga agtgtttgtt tatgtcaggg   900
ctcagtgagg tccagctgaa ccatatggat gatcacactc taccaggaa gtatggtatt   960
ggatttacca acatggtgga aaggaccacg cccggcagca aagatctctc cagtaaagaa  1020
tttcgtgaag gaggacgtat tctagtacag aaattacaga aatatcagcc acgaatagca  1080
gtgtttaatg gaaatgtat ttatgaaatt tttagtaaag aagttttttgg agtaaaggtt  1140
aagaacttgg aatttgggct tcagccccat aagattccag acacagaaac tctctgctat  1200
gttatgccat catccagtgc aagatgtgct cagtttcctc gagcccaaga caaagttcat  1260
tactacataa aactgaagga cttaagagat cagttgaaag gcattgaacg aaatatggac  1320
gttcaagagg tgcaatatac atttgaccta cagcttgccc aagaggatgc aaagaagatg  1380
gctgttaagg aagaaaaata tgatccaggt tatgaggcag catatggtgg tgcttacgga  1440
```

-continued

```
gaaaatccat gcagcagtga accttgtggc ttctcttcaa atgggctaat tgagagcgtg    1500
gagttaagag gagaatcagc tttcagtggc attcctaatg ggcagtggat gacccagtca    1560
tttacagacc aaattccttc ctttagtaat cactgtggaa cacaagaaca ggaagaagaa    1620
agccatgctt aagaatggtg cttctcagct ctgcttaaat gctgcagttt taatgcagtt    1680
gtcaacaagt agaacctcag tttgctaact gaagtgtttt attagtattt tactctagtg    1740
gtgtaattgt aatgtagaac agttgtgtgg tagtgtgaac cgtatgaacc taagtagttt    1800
ggaagaaaaa gtagggtttt tgtatactag cttttgtatt tgaattaatt atcattccag    1860 cttttttatat actatatttc atttatgaag aaattgattt tcttttggga gtcactttta    1920
atctgtaatt ttaaaataca agtctgaata tttatagttg attcttaact gtgcataaac    1980
ctagatatac cattatccct tttataccta agaagggcat gctaataatt accactgtca    2040
aagaggcaaa ggtgttgatt tttgtatata agttaagcct cagtggagtc tcatttgtta    2100
gtttttagtg gtaactaagg gtaaactcag ggttccctga gctatatgca cactcagacc    2160
tctttgcttt accagtggtg tttgtgagtt gctcagtagt aaaaactggc ccttacctga    2220
cagagccctg gctttgacct gctcagccct gtgtgttaat cctctagtag ccaattaact    2280
actctggggt ggcaggttcc agagaatcga gtagaccttt tgccactcat ctgtgtttta    2340
cttgagacat gtaaatatga tagggaagga actgaatttc tccattcata tttataacca    2400
ttctagtttt atcttccttg gctttaagag tgtgccatgg aaagtgataa gaaatgaact    2460
tctaggctaa gcaaaaagat gctggagata tttgatactc tcatttaaac tggtgcttta    2520
tgtacatgag atgtactaaa ataagtaata tagaattttt cttgctaggt aaatccagta    2580
agccaataat tttaaagatt cttttatctgc atcattgctg tttgttacta taaattaaat    2640
gaacctcatg gaaaggttga ggtgtatacc tttgtgattt tctaatgagt tttccatggt    2700
gctacaaata atccagacta ccaggtctgg tagatattaa agctgggtac taagaaatgt    2760
tatttgcatc ctctcagtta ctcctgaata ttctgatttc atacgtaccc agggagcatg    2820
ctgttttgtc aatcaatata aaatatttat gaggtctccc ccaccccag gaggttatat     2880 gattgctctt ctctttataa taagagaaac aaattcttat tgtgaatctt aacatgcttt    2940
ttagctgtgg ctatgatgga ttttattttt tcctaggtca agctgtgtaa aagtcattta    3000
tgttatttaa atgatgtact gtactgctgt ttacatggac gttttgtgcg ggtgctttga    3060
agtgccttgc atcagggatt aggagcaatt aaattatttt ttcacgggac tgtgtaaagc    3120
atgtaactag gtattgcttt ggtatataac tattgtagct ttacaagaga ttgtttatt    3180 tgaatgggga aaatacccct taaattatga cggacatcca ctagagatgg gtttgaggat    3240
tttccaagcg tgtaataatg atgttttcc taacatgaca gatgagtagt aaatgttgat     3300
atatcctata catgacagtg tgagactttt tcattaaata atattgaaag attttaaaat    3360
tcatttgaaa gtctgatggc ttttacaata aaagatatta agaattgtta                3410
```

<210> SEQ ID NO 10
<211> LENGTH: 410
<212> TYPE: PRT
<213> ORGANISM: Homo sapiens
<220> FEATURE:
<221> NAME/KEY: VARIANT
<222> LOCATION: (91)..(91)
<223> OTHER INFORMATION: Applicants herein disclose a Pro to Ser variant
      at this amino acid position

<400> SEQUENCE: 10

-continued

```
Met Glu Ala Glu Asn Ala Gly Ser Tyr Ser Leu Gln Gln Ala Gln Ala
 1               5                  10                  15

Phe Tyr Thr Phe Pro Phe Gln Gln Leu Met Ala Glu Ala Pro Asn Met
            20                  25                  30

Ala Val Val Asn Glu Gln Gln Met Pro Glu Glu Val Pro Ala Pro Ala
         35                  40                  45

Pro Ala Gln Glu Pro Val Gln Glu Ala Pro Lys Gly Arg Lys Arg Lys
     50                  55                  60

Pro Arg Thr Thr Glu Pro Lys Gln Pro Val Glu Pro Lys Lys Pro Val
 65              70                  75                  80

Glu Ser Lys Lys Ser Gly Lys Ser Ala Lys Ser Lys Glu Lys Gln Glu
                 85                  90                  95

Lys Ile Thr Asp Thr Phe Lys Val Arg Lys Val Asp Arg Phe Asn
                100                 105                 110

Gly Val Ser Glu Ala Glu Leu Leu Thr Lys Thr Leu Pro Asp Ile Leu
            115                 120                 125

Thr Phe Asn Leu Asp Ile Val Ile Gly Ile Asn Pro Gly Leu Met
130                 135                 140

Ala Ala Tyr Lys Gly His His Tyr Pro Gly Pro Gly Asn His Phe Trp
145             150                 155                 160

Lys Cys Leu Phe Met Ser Gly Leu Ser Glu Val Gln Leu Asn His Met
                165                 170                 175

Asp Asp His Thr Leu Pro Gly Lys Tyr Gly Ile Gly Phe Thr Asn Met
            180                 185                 190

Val Glu Arg Thr Thr Pro Gly Ser Lys Asp Leu Ser Ser Lys Glu Phe
        195                 200                 205

Arg Glu Gly Gly Arg Ile Leu Val Gln Lys Leu Gln Lys Tyr Gln Pro
    210                 215                 220

Arg Ile Ala Val Phe Asn Gly Lys Cys Ile Tyr Glu Ile Phe Ser Lys
225                 230                 235                 240

Glu Val Phe Gly Val Lys Val Lys Asn Leu Glu Phe Gly Leu Gln Pro
                245                 250                 255

His Lys Ile Pro Asp Thr Glu Thr Leu Cys Tyr Val Met Pro Ser Ser
            260                 265                 270

Ser Ala Arg Cys Ala Gln Phe Pro Arg Ala Gln Asp Lys Val His Tyr
        275                 280                 285

Tyr Ile Lys Leu Lys Asp Leu Arg Asp Gln Leu Lys Gly Ile Glu Arg
    290                 295                 300

Asn Met Asp Val Gln Glu Val Gln Tyr Thr Phe Asp Leu Gln Leu Ala
305                 310                 315                 320

Gln Glu Asp Ala Lys Lys Met Ala Val Lys Glu Lys Tyr Asp Pro
                325                 330                 335

Gly Tyr Glu Ala Ala Tyr Gly Gly Ala Tyr Gly Glu Asn Pro Cys Ser
            340                 345                 350

Ser Glu Pro Cys Gly Phe Ser Ser Asn Gly Leu Ile Glu Ser Val Glu
        355                 360                 365

Leu Arg Gly Glu Ser Ala Phe Ser Gly Ile Pro Asn Gly Gln Trp Met
    370                 375                 380

Thr Gln Ser Phe Thr Asp Gln Ile Pro Ser Phe Ser Asn His Cys Gly
385                 390                 395                 400

Thr Gln Glu Gln Glu Glu Ser His Ala
                405                 410
```

```
<210> SEQ ID NO 11
<211> LENGTH: 307
<212> TYPE: PRT
<213> ORGANISM: Homo sapiens
<220> FEATURE:
<221> NAME/KEY: NON_TER
<222> LOCATION: (1)..(1)
<223> OTHER INFORMATION: functional N-terminal deletion mutant of hMBD4
      (SEQ ID N0:2); aa no. 1 corresponds to aa no. 274 of hMBD4; mutant
      shows enhanced deglycosylase specificity towards CpG dinucleotide
      sequences; see Zhu et al. Nuc. Acid Res. 28:4157-4165, 2000.

<400> SEQUENCE: 11

Glu Ser Glu Pro Val Ala Gln Lys Ser Gln Leu Asp Arg Thr Val Cys
1               5                   10                  15

Ile Ser Asp Ala Gly Ala Cys Gly Glu Thr Leu Ser Val Thr Ser Glu
            20                  25                  30

Glu Asn Ser Leu Val Lys Lys Glu Arg Ser Leu Ser Ser Gly Ser
            35                  40                  45

Asn Phe Cys Ser Glu Gln Lys Thr Ser Gly Ile Ile Asn Lys Phe Cys
    50                  55                  60

Ser Ala Lys Asp Ser Glu His Asn Glu Lys Tyr Glu Asp Thr Phe Leu
65                  70                  75                  80

Glu Ser Glu Glu Ile Gly Thr Lys Val Glu Val Val Glu Arg Lys Glu
                85                  90                  95

His Leu His Thr Asp Ile Leu Lys Arg Gly Ser Glu Met Asp Asn Asn
            100                 105                 110

Cys Ser Pro Thr Arg Lys Asp Phe Thr Gly Glu Lys Ile Phe Gln Glu
        115                 120                 125

Asp Thr Ile Pro Arg Thr Gln Ile Glu Arg Arg Lys Thr Ser Leu Tyr
    130                 135                 140

Phe Ser Ser Lys Tyr Asn Lys Glu Ala Leu Ser Pro Arg Arg Lys
145                 150                 155                 160

Ala Phe Lys Lys Trp Thr Pro Pro Arg Ser Pro Phe Asn Leu Val Gln
                165                 170                 175

Glu Thr Leu Phe His Asp Pro Trp Lys Leu Leu Ile Ala Thr Ile Phe
            180                 185                 190

Leu Asn Arg Thr Ser Gly Lys Met Ala Ile Pro Val Leu Trp Lys Phe
        195                 200                 205

Leu Glu Lys Tyr Pro Ser Ala Glu Val Ala Arg Thr Ala Asp Trp Arg
    210                 215                 220

Asp Val Ser Glu Leu Leu Lys Pro Leu Gly Leu Tyr Asp Leu Arg Ala
225                 230                 235                 240

Lys Thr Ile Val Lys Phe Ser Asp Glu Tyr Leu Thr Lys Gln Trp Lys
                245                 250                 255

Tyr Pro Ile Glu Leu His Gly Ile Gly Lys Tyr Gly Asn Asp Ser Tyr
            260                 265                 270

Arg Ile Phe Cys Val Asn Glu Trp Lys Gln Val His Pro Glu Asp His
        275                 280                 285

Lys Leu Asn Lys Tyr His Asp Trp Leu Trp Glu Asn His Glu Lys Leu
    290                 295                 300

Ser Leu Ser
305

<210> SEQ ID NO 12
<211> LENGTH: 202
<212> TYPE: PRT
```

<213> ORGANISM: Homo sapiens
<220> FEATURE:
<221> NAME/KEY: NON_TER
<222> LOCATION: (1)..(1)
<223> OTHER INFORMATION: functional N-terminal deletion mutant of hMBD4
(SEQ ID N0:2); aa no. 1 corresponds to aa no. 379 of hMBD4
protein; mutant shows enhanced deglycosylase specificity towards
CpG dinucleotide sequences; see Zhu et al. Nuc. Acid Res.
28:4157-4165, 2000.

<400> SEQUENCE: 12

```
Gly Ser Glu Met Asp Asn Asn Cys Ser Pro Thr Arg Lys Asp Phe Thr
1               5                   10                  15

Gly Glu Lys Ile Phe Gln Glu Asp Thr Ile Pro Arg Thr Gln Ile Glu
            20                  25                  30

Arg Arg Lys Thr Ser Leu Tyr Phe Ser Ser Lys Tyr Asn Lys Glu Ala
        35                  40                  45

Leu Ser Pro Pro Arg Arg Lys Ala Phe Lys Lys Trp Thr Pro Pro Arg
    50                  55                  60

Ser Pro Phe Asn Leu Val Gln Glu Thr Leu Phe His Asp Pro Trp Lys
65                  70                  75                  80

Leu Leu Ile Ala Thr Ile Phe Leu Asn Arg Thr Ser Gly Lys Met Ala
                85                  90                  95

Ile Pro Val Leu Trp Lys Phe Leu Glu Lys Tyr Pro Ser Ala Glu Val
            100                 105                 110

Ala Arg Thr Ala Asp Trp Arg Asp Val Ser Glu Leu Leu Lys Pro Leu
        115                 120                 125

Gly Leu Tyr Asp Leu Arg Ala Lys Thr Ile Val Lys Phe Ser Asp Glu
    130                 135                 140

Tyr Leu Thr Lys Gln Trp Lys Tyr Pro Ile Glu Leu His Gly Ile Gly
145                 150                 155                 160

Lys Tyr Gly Asn Asp Ser Tyr Arg Ile Phe Cys Val Asn Glu Trp Lys
                165                 170                 175

Gln Val His Pro Glu Asp His Lys Leu Asn Lys Tyr His Asp Trp Leu
            180                 185                 190

Trp Glu Asn His Glu Lys Leu Ser Leu Ser
        195                 200
```

<210> SEQ ID NO 13
<211> LENGTH: 147
<212> TYPE: PRT
<213> ORGANISM: Homo sapiens
<220> FEATURE:
<221> NAME/KEY: NON_TER
<222> LOCATION: (1)..(1)
<223> OTHER INFORMATION: functional N-terminal deletion mutant of hMBD4
(SEQ ID N0:2); aa no. 1 corresponds to aa no. 434 of hMBD4
protein; mutant shows enhanced deglycosylase specificity towards
CpG dinucleotide sequences; see Zhu et al. Nuc. Acid Res.
28:4157-4165, 2000.

<400> SEQUENCE: 13

```
Ala Phe Lys Lys Trp Thr Pro Pro Arg Ser Pro Phe Asn Leu Val Gln
1               5                   10                  15

Glu Thr Leu Phe His Asp Pro Trp Lys Leu Leu Ile Ala Thr Ile Phe
            20                  25                  30

Leu Asn Arg Thr Ser Gly Lys Met Ala Ile Pro Val Leu Trp Lys Phe
        35                  40                  45

Leu Glu Lys Tyr Pro Ser Ala Glu Val Ala Arg Thr Ala Asp Trp Arg
    50                  55                  60
```

-continued

```
Asp Val Ser Glu Leu Leu Lys Pro Leu Gly Leu Tyr Asp Leu Arg Ala
 65                  70                  75                  80

Lys Thr Ile Val Lys Phe Ser Asp Glu Tyr Leu Thr Lys Gln Trp Lys
             85                  90                  95

Tyr Pro Ile Glu Leu His Gly Ile Gly Lys Tyr Gly Asn Asp Ser Tyr
            100                 105                 110

Arg Ile Phe Cys Val Asn Glu Trp Lys Gln Val His Pro Glu Asp His
        115                 120                 125

Lys Leu Asn Lys Tyr His Asp Trp Leu Trp Glu Asn His Glu Lys Leu
    130                 135                 140

Ser Leu Ser
145
```

DISCOVERY AND DIAGNOSTIC METHODS USING 5-METHYLCYTOSINE DNA GLYCOSYLASE

TECHNICAL FIELD OF THE INVENTION

The present invention relates to DNA methylation, to methods for identification of methylated, and/or potentially methylatable CpG dinucleotides in genomic DNA sequences, and to methods of isolating genomic DNA sequences comprising methylated CpG dinucleotide sequences. The present invention relates to methods for comparison of the methylation state of specific CpG dinucleotides, and of patterns thereof between and among normal and diseased genomic DNA samples, and to methods for determining all potentially methylatable CpG dinucleotides in genomic DNA samples. The present invention relates to novel uses of 5-methylcytosine DNA glycosylase in combination with art-recognized DNA repair enzymes (e.g., DNA methyltransferase), to specifically label CpG dinucleotides corresponding to $^{M}$CpG sequences in genomic DNA sequences.

BACKGROUND OF THE INVENTION

The identification of early genetic changes in tumorigenesis is a primary focus in molecular cancer research. Characterization of the nature and pattern of cancer-associated genetic alterations will allow for early detection, diagnosis and treatment of cancer. Such genetic alterations in vertebrates fall generally into one of three categories: gain or loss of genetic material; mutation of genetic material; or methylation at cytosine residues in CpG dinucleotides within "CpG islands." Among these, DNA methylation is unique in that it is a mechanism for modifying the base sequence of DNA without altering its coding, and because it is a heritable reversible epigenetic change. Changes in methylation state are also known to affect gene expression (e.g., transcriptional initiation of genes where CpG islands located at or near the promoter region) or genomic stability. DNA methylation plays a role in gene inactivation, cell differentiation, tumorigenesis, X-chromosome inactivation, genomic imprinting, and is required for mammalian development (Li, et al., *Cell* 69:915-926, 1992; Okano et al., *Cell* 99:247-57, 1999).

DNA methylation in higher-order eukayotic organisms. In higher order eukaryotic organisms, DNA is methylated only at cytosines located 5' to guanosine in the CpG dinucleotide. This modification has important regulatory effects on gene expression predominantly when it involves CpG rich areas (CpG islands) located in the promoter region of a gene sequence. Gene silencing through DNA methylation has been shown to be a major transcriptional regulatory mechanism in mammalian, plant and fungal systems (Colot and Rossignol, *Bioessays* 21:402-1, 1999). Hypermethylation of promotor regions on DNA have been correlated with the progression of cancer (Jones & Laird, *Nat. Genet.* 21:163-7, 1999) and the etiology of aging (Ahuja et al., *Cancer Res.* 58:5489-94, 1998). Extensive methylation of CpG islands has been associated with transcriptional inactivation of selected imprinted genes and genes on the inactive X chromosome of females. Aberrant methylation of normally unmethylated CpG islands has been described as a frequent event in immortalized and transformed cells and has been frequently associated with transcriptional inactivation of tumor suppressor genes in human cancers.

The exact mechanisms of DNA methylation and demethylation have not been determined, although recently discovered methyltransferases, demethylases and methyl-CpG binding proteins (Amir et al., *Nat. Genet.* 23:185-8, 1999; Okano et al., *Cell* 99:247-57, 1999) will increase understanding of these processes. These DNA binding proteins and enzymes thus use 5-methylcytosine in DNA as a key recognition signal to mediate transcriptional regulation. DNA cytosine methylation is a post-replicative process catalyzed by DNA methyltransferases whereas demethylation or removal of 5-methylcytosine from DNA occurs most likely through the action of specific DNA glycolsylases.

DNA methyltransferases. Mammalian cells possess methylases that methylate cytosine residues on DNA that are 5' neighbors of guanine in CpG dinucleotides (CpG). Methylation occurs after cytosine has been incorporated into DNA in a process catalyzed by DNA methyltransferases ("Dnmts") which transfer the methyl group from S-adenosylmethionine to the 5'-position of the pyrimidine ring in, characteristically but not exclusively, the context of the palindromic CpG dinucleotide (Ramsahoye et al., *Proc Natl Acad Sci USA.* 97:5237-42, 2000). 5-Methylcytosine is asymmetrically distributed in the genome and is most commonly found in CpG-poor regions, since most CpG islands in somatic cells remain methylation-free, except for the promoters of imprinted genes and genes on the inactive X-chromosome (Bird et al., *Cell* 40:91-99, 1985) where methylation of 5' regulatory regions can lead to transcriptional repression.

Three Dnmt enzymes are known in mouse and human, and these have overlapping yet distinct abilities to methylate "hemimethylated" and completely unmethylated CpG dinucleotide pairs (i.e., "maintenance" and "de novo" methylation, respectively). Hemi-methylation is defined as a state in which the two opposing cytosines on either DNA strand in a single palindromic CpG dinucleotide differ in that one is methylated at the C-5 position, and the other is not.

The predominant Dnmt in the cell, Dnmt1, was cloned and characterized by Bestor and colleagues (Bestor et al., *J. Mol. Biol.* 203:971-83, 1988; Bestor, *Gene,* 74:9-12, 1988) and is localized to replication machines in the S-phase nucleus (Leonhardt et al., *Cell* 71:865-73, 1992; Rountree et el., *Nat. Genet* 25:269-77, 2000). Since Dnmt1 shows a preference for hemimethylated CpG pairs (Gruenbaum et al., *FEBS Lett.* 124:67-71, 1981; Bestor and Ingram, *Proc Natl Acad Sci USA.* 80:5559-63, 1983), it is considered to be an excellent candidate for copying the pattern of methylation present on the parental strand after DNA has been replicated (i.e, "maintenance" methylation). However, Dnmt1 is capable of modifying unmethylated DNA in the test tube, and is thus also a candidate for inducing de novo methylation. The recently discovered Dnmts, Dnmt3a and 3b (Okano et al., *Nucleic Acids Res.* 26:2536-40, 1998) show equal activities in vitro for unmethylated and hemimethylated substrates, and have been shown to be capable of de novo methylation of transfected DNA in culture (Hsieh, *Mol Cell Biol.* 19:8211-8, 1999) and in *Drosophila* (Lyko et al., *Nat. Genet.* 23:363-6, 1999). Interestingly, satellite DNAs appear to be a preferred target for the human DNMT3B enzyme, because these satellite DNA sequences are specifically undermethylated in patients with ICF syndrome, characterized by germ-line mutations in the DNMT3B gene (Hansen et al., *Proc Natl Acad Sci USA.* 96:14412-7, 1999; Okano et al., *Cell* 99:247-57, 1999; Xu et al., *Nature* 402:187-91., 1999).

DNA glycosylases. Base excision repair (BER) occurs in vivo to repair DNA base damage involving relatively minor disturbances in the helical DNA structure, such as deaminated, oxidized, alkylated or absent bases. Numerous DNA glycosylases are known in the art, and function in vivo during BER to release damaged or modified bases by cleavage of the glycosidic bond linking such bases to the sugar-phosphate backbone of DNA (see Memisoglu & Samson, *Mutation Research* 451:39-51, 2000). All DNA glycosylases cleave gylcosidic bonds, but differ in their base substrate specificity and in their reaction mechanisms. Moreover a subset of DNA glycosylases possess an additional apurinic/apyrimidinic (AP) lyase activity, and one DNA glycosylsase (Ogg1) has an associated DNA deoxyribophosphatase acitivity (Sandigursky et al., *Nucleic Acids Res.* 25:4557-4561, 1997).

The recently described enzyme 5-methylcytosine DNA glycosylase (5-MCDG) provides a potential mechanism for demethylation of methylcytosine residues in DNA. Specifically, 5-MCDG acts by cleaving glycosylic bonds at methylated CpG sites of DNA, removing 5-methylcytosine (5-MeC) from the DNA backbone as a free base (Wolffe et al., *Proc. Nat. Acad. Sci. USA* 96:5894-5896, 1999).

Two types of 5-MCDG enzymes have been described. One type, found in both humans and chicken, comprises bi-functional enzymes having both G/T mismatch as well as 5-MCDG activity (Zhu et al., *Proc. Natl. Acad. Sci. USA* 98:5031-6, 2001; Zhu et al., *Nuc. Acid Res.* 28:4157-4165, 2000; and Neddermann et al., *J.B.C.* 271:12767-74, 1996). The other type (substantially purified from human sources) corresponds to a mono-functional enzyme having only 5-MCDG activity (Vairapandi & Duker, *Oncogene* 13:933-938, 1996; Vairapandi et al., *J. Cell. Biochem.* 79:249-260, 2000).

The mono-functional human version of 5-methylcytosine DNA glycosylase cleaves DNA specifically at fully methylated CpG sites, and is inactive on hemimethylated DNA (Vairapandi & Duker, supra; Vairapandi et al., supra), in contrast to the above-mentioned bi-functional enzymes. A recombinant version of the bi-functional chick embryo 5-methylcytosine-DNA glycolsylase has a greater activity for hemimethylated DNA than for fully methylated DNA, but its relative activity may be potentiated by the addition of recombinant CpG-rich RNA, ATP and the enzyme RNA helicase (Zhu et al., supra).

The mono-functional human 5-methylcytosine DNA glycosylase activity is associated with such accessory factors as the nuclear protein, proliferating cell nuclear antigen (PCNA) (Vairpandi et al). The DNA glycosylase activity may require an RNA component for full enzyme activity, however the activity is apparently insensitive to RNAse treatment (Vairpandi et al; Swisher et al., *Nuc. Acid Res.* 26:5573-5580, 1998).

Limitations of the Art. Changes in global levels of methylation and regional changes in patterns of methylation (e.g., CpG islands), are among the earliest and most frequently observed events known in many human cancers. For this reason, the activity of DNA methylases, and knowledge of methylation patterns can provide an early screen for cancer detection.

There are various art-recognized assays for assessing the methylation state at particular CpG sequences, once the sequence region comprising them has been identified so that specific primers and/or probes can be constructed. Such assays include: DNA sequencing methods; Southern blotting methods; MethyLight™ (fluorescence-based real-time PCR technique described by Eads et al., *Cancer Res.* 59:2302-2306, 1999; U.S. Pat. No. 6,331,393); MS-SNuPE (Methylation-sensitive Single Nucleotide Primer Extension assay described by Gonzalgo & Jones, *Nucleic Acids Res.* 25:2529-2531, 1997; U.S. Pat. No. 6,251,594); MSP (Methylation-specific PCR assay described by Herman et al. *Proc. Natl. Acad. Sci. USA* 93:9821-9826, 1996; U.S. Pat. No. 5,786,146); and COBRA (Combined Bisulfite Restriction Analysis methylation assay described by Xiong & Laird, *Nucleic Acids Res.* 25:2532-2534, 1997). Such methylation assays are used, for example, to analyze genomic DNA sequence regions that exhibit altered methylation patterns (hypermethylation or hypomethylation) in cancer patients. These methylation-altered DNA sequences are, in turn, useful in indirect therapeutic applications as diagnostic, prognostic and therapeutic markers for human cancer.

Assays for the discovery of novel differentially methylated CpG sequences are less numerous in the art, but include such methods as: restriction landmark genomic scanning ("RLGS"; Eng et al., *Nature Genetics* 25:101-102, 2000; Costello et al., *Nature Genetics* 25:132-138, 2000; Zhu et al., *Proc. Natl. Acad. Sci. USA* 96:8058-8063, 1999); methylated CpG island amplification ("MCA"; Toyota et al., *Cancer Res.* 59:2307-2312, 1999; WO 00/26401A1), differential methylation hybridization ("DMH"; Yan et al., *Clin. Canc. Res.* 6:1432-1438, 2000); arbitrarily primed-polymerase chain reaction ("AP-PCR"; Liang et al., *Genomics* 53:260-268, 1998); and RLGS in combination with virtual genome scans ("VGS"; Rouillard et al., *Genome Research* 11:1453-1459, 2001) derived from the sequence of the human genome to predict sequence of RLGS fragments (spots).

Restriction Landmark Genomic Scanning. For example, restriction landmark genomic scanning ("RLGS") approaches have been employed to identify sequences and regions of differential methylation, and regions so-identified have been cloned and sequenced. RLGS methods take advantage of the fact that specific DNA cleavage by particular restriction enyzmes, such as NotI is methylation sensitive. Moreover, NotI has a CG-rich octanucleotide recognition motif, and cleaves predominantly in CpG-rich "islands." Thus, digestion of genomic DNA with NotI and end-labeling of the NotI staggered ends, followed by further restriction digestion (e.g., with 5-base and/or 6-base recognition sequence enzymes) in combination with 2-dimensional electrophoresis has been used to generate resolved patterns of CpG-island-related fragments having at least one labeled NotI end. Such patterns can be used to compare the methylation status among various genomic DNA samples, and if a particular NotI site is methylated in a test genomic DNA sample, relative to that in normal genomic DNA, no corresponding end labeled fragment(s) will be visible in the RLGS pattern of the test sample (corresponding 'spot disappearance,' or absence). Boundary libraries (e.g., of NotI-EcoRV fragments) can then be used to obtain cloned DNA corresponding to such regions.

Significantly, however, such prior art RLGS methods for detection of CpG methylation are limited, inter alia, by: (i) the use of only particular methylation-sensitive restriction enzymes, which effectively limits analyses to CpG sequences within CpG island regions; (ii) dependence (for detection) upon NotI end-labeling (or the equivalent); and (iii) upon the disappearance of (more accurately, the absence of) a test DNA spot (i.e., where a particular NotI site in a test DNA sample is methylated and therefore not cleaved by NotI digestion) relative to a corresponding spot present in the normal (test) DNA 2-dimensional pattern. Moreover the current boundary libraries have 'holes,' because the EcoRV-EcoRV fragments are excluded.

Virtual Genome Scans. Virtual genome scans (VGS) provide methods for use in conjunction with RGLS methods to identify fragments of interest displayed in RLGS scans. Informatics tools are used, in conjunction with known human genome sequence information, to produce virtual scans, for example, with NotI and EcoRV (as first-dimension RLGS restriction enzymes), and, for example, HinfI or DpnII (as second-dimension enzymes). The size of the expected NotI-EcoRV and NotI-NotI fragments (if no intervening EcoRV site is present) are computed, along with the second-dimension fragments, based on the HinfI or DpnII site nearest to a particular NotI site (Rouillard et al. *Genome Research* 11:1453-1459, 2001). Thus, identification of RLGS sequences can be made without the use of boundary libraries, and is therefore not subject to the EcoRV-EcoRV 'holes' present in such libraries.

However, the method still depends on determining the differences between two samples using RLGS, and is thus is subject most of the limitations thereof.

Methylated CpG Island Amplification. Methylated CpG island amplification ("MCA") is a PCR-based technique for rapid enrichment of hypermethylated CG-rich regions, that requires the sequential digestion by a particular methylation sensitive, methylation insensitive isoschizomeric enzyme pair (i.e., SmaI and XmaI, respectively), followed by PCR amplification based on primers that specifically hybridize to adapters ligated to the staggered XmaI ends. Additionally, the restriction sites must be closely situated (<1 kb apart). Thus, as in the case of prior art RLGS applications, the method is primarily limited to particular CpG sequences within CpG-rich genomic regions (Toyota et al., *Cancer Res.* 59:2307-2312, 1999). Moreover, and the technique is sensitive to artifacts relating to incomplete digestion with SmaI, the methylation sensitive restriction enzyme. The technique can be combined, in a more complex multistep method with substractive hybridization (RDA; representational difference analysis) to obtain cloned fragments enriched for hypermethylated sequences (Id).

Methylation-Sensitive Arbitrarily Primed PCR. Likewise, methylation-sensitive arbitrarily primed-polymerase chain reaction ("AP-PCR") is a PCR-based technique for rapid enrichment of hypermethylated CG-rich regions, that involves co-digestion of DNA with a methylation-insensitive enzyme (e.g., RsaI) to generally reduce the size of DNA fragments, plus, in separate reactions, a methylation-sensitive member, and a methylation-insensitive member of a isoschizomeric enzyme pair (e.g., RsaI plus HpaII, and RsaI plus MspI, respectively), followed by PCR amplification using one or more specific oligonucleotide primers. In this case, no PCR products are produced if the region between two primer sites contains an unmethylated HpaII (CCGG) sequence. Digestion of the DNA with RsaI only, and with RsaI and MspI serve as controls for determining whether bands observed in the AP-PCR of RsaI- plus HpaII-digested DNA are actually due to differential methylation of CCGG sequences within the region of amplification (Gonzalgo et al., *Cancer Research* 57:594-599).

Thus, methylation-sensitive AP-PCR methods, are limited commensurate with primer choice, and as for RLGS and MCA described above, are primarily biased toward CpG island regions, especially when extensively CG-rich primer sequences are employed (Liang et al., *Genomics* 53:260-268, 1998). Generally, methylation-sensitive AP-PCR is subject to many of the same artifacts that limit the effectiveness of MCA methods, such as incomplete digestion by restriction enzymes, and distance between primer sites.

Differential Methylation Hybridization. Differential methylation hybridization ("DMH") is a micro array-based method involving differential probing of arrayed CG-rich tags (from a CpG island genomic library) with amplicons from a reference, or, e.g., tumor DNA samples. The differences in tumor and reference signal intensities on the tested CpG island arrays reflect methylation alterations of corresponding sequences in the tumor DNA (Yan et al., *Clin. Canc. Res.* 6:1432-1438, 2000).

To produce amplicons, the DNA is digested to produce small (<200 bp) DNA fragments while preserving CpG islands (e.g., by digestion with MseI, recognizing TTAA). Linkers are ligated to the fragment ends, and the fragments are digested with a methylation-sensitive enzyme, e.g., BstUI (77% of known CpG islands contain BstUI sites), prior to filling in the protruding linker ends and PCR amplification using linker primers. Fragments cleaved by the methylation-sensitive enzyme are rendered non-amplifiable by the linker primers, so that the amplified fragment pool is enriched for methylated amplicons.

However, the method is limited to CpG-rich islands, and at least currently, is further limited by the fact that only about 2% of the total genomic CpG island regions are represented in the available arrayed panels (Id).

Whereas RLGS and other prior art assays to identify differentially methylated CpG sequences have great potential there is a need in the art for additional methods not only to validate the number of genes with hypermethylated promoters in neoplasia and other diseases, but also to determine the number that are relevant to tumorigenesis or other aberrant cell functions. For example, many promoters, including those critical to cancer biology and inactivated through hypermethylation, do not contain CpG islands.

Therefore, there is a need in the art for novel methods to identify all novel differentially methylated CpG dinucleotide sequences, where the methods are neither limited to methylation analyses within CpG-rich genomic regions (as is primarily the case for RLGS, AP-PCR, MCA, and DMH applications), nor limited to methylation analyses of CpG dinucleotide sequences within particular restriction enzymes recognition motifs. Additionally, there is a need in the art for methods which provide for positive detection of methylated genomic DNA fragments based on specific labeling of methylated CpG sequences, as opposed to methods based on differential digestion by a methylation-sensitive restriction enzyme followed by indirect or negative detection, based on labeling of restriction enzyme generated ends and identification by virtue of the absence of labeling (as in RLGS methods). Additionally, there is a need in the art to identify those CpG dinucleotide sequences that are potentially methylatable, either at the level of isolated genomic DNA, or at the cellular level in the context of particular cellular physiologies.

SUMMARY OF THE INVENTION

Applicant herein discloses novel uses of 5-methylcytosine DNA glycosylase, in combination with art-recognized DNA repair enzymes, and in particular embodiments with DNA methyltransferase, to specifically label cytosine bases in methylated CpG dinucleotides in genomic DNA sequences. Such labeling occurs through enzymatic substitution of 5-methylcytosine with labeled cytosine, and allows, inter alia, for selection and cloning of sequences originally containing methylated CpG dinucleotides.

Particular embodiments of the present invention provide methods for identification of methylated, and/or potentially methylatable CpG dinucleotides in genomic DNA sequences. Sequences comprising such methylated, and/or potentially methylatable CpG dinucleotides may be cloned, sequenced, and/or mapped within the genome to provide useful methylation markers.

Additional embodiments provide methods for comparison of the methylation state of specific CpG dinucleotides, and of patterns thereof between normal and diseased genomic DNA samples.

Further embodiments provide methods for determining all potentially methylatable CpG dinucleotides in genomic DNA samples, or for differentially labeling existing $^M$CpG, and potentially methylatable CpG dinucleotide sequences in isolated or cellular genomic DNA.

Yet further embodiments provide methods for selectively isolating genomic DNA fragments corresponding to methylated CpG-containing genomic DNA fragments.

As will be obvious to those skilled in the relevant art, the present invention includes, but is not limited to the those embodiments disclosed herein below, which describe and teach particular preferred implementations of the invention in the context of various resolution and analytical methods, including RLGS, VGS and microarray hybridization.

The present invention provides methods for specifically labeling CpG sequences corresponding to methylated CpG sequences in an isolated genomic DNA sample, comprising: obtaining a sample of isolated genomic DNA; digesting the isolated genomic DNA with a restriction endonuclease to produce genomic DNA fragments; treating the genomic DNA fragments with 5-methylcytosine deglycosylase, whereby one or more 5-methylcytosine bases are removed to produce abasic genomic DNA fragments; and treating the abasic genomic DNA fragments with base excision repair (BER) enzymes in the presence of labeled dCTP, whereby 5-methylcytosine removed from the genomic DNA fragments by 5-methylcytosine deglycosylase is replaced by labeled cytosine in the one or more corresponding positions of the abasic genomic DNA fragments to produce labeled genomic DNA fragments.

The present invention also provides methods for comparing the CpG methylation status, extend or pattern between or among reference and test genomic DNA samples, comprising: obtaining a reference and a test sample of isolated genomic DNA; digesting the respective isolated genomic DNA samples with one or more restriction endonucleases to produce genomic DNA fragments; treating the respective genomic DNA fragments with 5-methylcytosine deglycosylase, whereby one or more 5-methylcytosine bases are removed to produce abasic genomic DNA fragments; treating the respective abasic genomic DNA fragments with base excision repair (BER) enzymes in the presence of labeled dCTP, whereby 5-methylcytosine removed from the genomic DNA fragments by 5-methylcytosine deglycosylase is replaced by labeled cytosine in the one or more corresponding positions of the abasic genomic DNA fragments to produce labeled genomic DNA fragments; resolving, at least in part, the respective labeled genomic DNA fragments; and detecting the respective methylated nucleic acid fragments based on the presence of the label, whereby a comparison of status, extent, or pattern of CpG methylation is enabled.

Additionally, the present invention provides methods for selective isolation of genomic DNA fragments corresponding to methylated CpG-containing genomic DNA fragments, comprising: obtaining a sample of isolated genomic DNA; digesting the isolated genomic DNA sample with one or more restriction endonucleases to produce genomic DNA fragments; treating the genomic DNA fragments with 5-methylcytosine deglycosylase to remove one or more 5-methylcytosine bases to produce abasic genomic DNA fragments; treating the abasic genomic DNA fragments with base excision repair (BER) enzymes in the presence of labeled dCTP, whereby 5-methylcytosine removed from the genomic DNA fragments by 5-methylcytosine deglycosylase is replaced by labeled cytosine in the one or more corresponding positions of the abasic genomic DNA fragments to produce labeled genomic DNA fragments; and isolating the labeled DNA fragments based on the presence of the label, whereby labeled DNA fragments are separated, at least in part, from non-labeled DNA fragments.

The present invention further provides methods for labeling potentially-methylatable CpG sequences in CpG-containing genomic DNA fragments, comprising: obtaining a sample of isolated genomic DNA; digesting the isolated genomic DNA sample with one or more restriction endonucleases to produce genomic DNA fragments; treating the genomic DNA fragments with DNA methyltransferase in the presence of a methyl donor to produce hypermethylated genomic DNA fragments; treating the hypermethylated genomic DNA fragments with 5-methylcytosine deglycosylase to remove one or more hypermethylated 5-methylcytosine bases to produce abasic genomic DNA fragments; treating the abasic genomic DNA fragments with base excision repair (BER) enzymes in the presence of labeled dCTP, whereby 5-methylcytosine removed from the genomic DNA fragments by 5-methylcytosine deglycosylase is replaced by labeled cytosine in the one or more corresponding positions of the abasic genomic DNA fragments to produce labeled genomic DNA fragments.

The present invention further provides methods for differentially labeling existing $^M$CpG Sequences, and potentially-methylatable CpG sequences in CpG-containing genomic DNA fragments, comprising: obtaining a sample of isolated genomic DNA; digesting the isolated genomic DNA sample with one or more restriction endonucleases to produce genomic DNA fragments; treating the genomic DNA fragments with 5-methylcytosine deglycosylase to remove one or more 5-methylcytosine bases to produce abasic genomic DNA fragments; treating the abasic genomic DNA fragments with base excision repair (BER) enzymes in the presence of dCTP labeled with a first label, whereby 5-methylcytosine removed from the genomic DNA fragments by 5-methylcytosine deglycosylase is replaced by labeled cytosine in the one or more corresponding positions of the abasic genomic DNA fragments to produce labeled genomic DNA fragments, and wherein the first label precludes transfer by DNA methyltransferases of a methyl group from S-adenosylmethionine to the 5'-position of the labeled cytosine; treating the labeled genomic DNA fragments with DNA methyltransferase in the presence of a methyl donor to produce hypermethylated labeled genomic DNA fragments; treating the hypermethylated labeled genomic DNA fragments with 5-methylcytosine deglycosylase to remove one or more hypermethylated 5-methylcytosine bases to produce abasic labeled genomic DNA fragments; and treating the abasic labeled genomic DNA fragments with base excision repair (BER) enzymes in the presence of dCTP labeled with a second label, whereby hypermethylated 5-methylcytosine removed from the hypermethylated labeled genomic DNA fragments by 5-methylcytosine deglycosylase is replaced by labeled cytosine in the one or more corresponding positions of the abasic labeled genomic DNA fragments to produce doubly-labeled genomic DNA fragments, and whereby the existing $^M$CpG sequences and the potentially-methylatable CpG sequences in the CpG-containing genomic DNA fragments are differentially labeled by the first and second labels, respectively, in the doubly-labeled genomic DNA fragments.

DETAILED DESCRIPTION OF THE INVENTION

Figure 1:
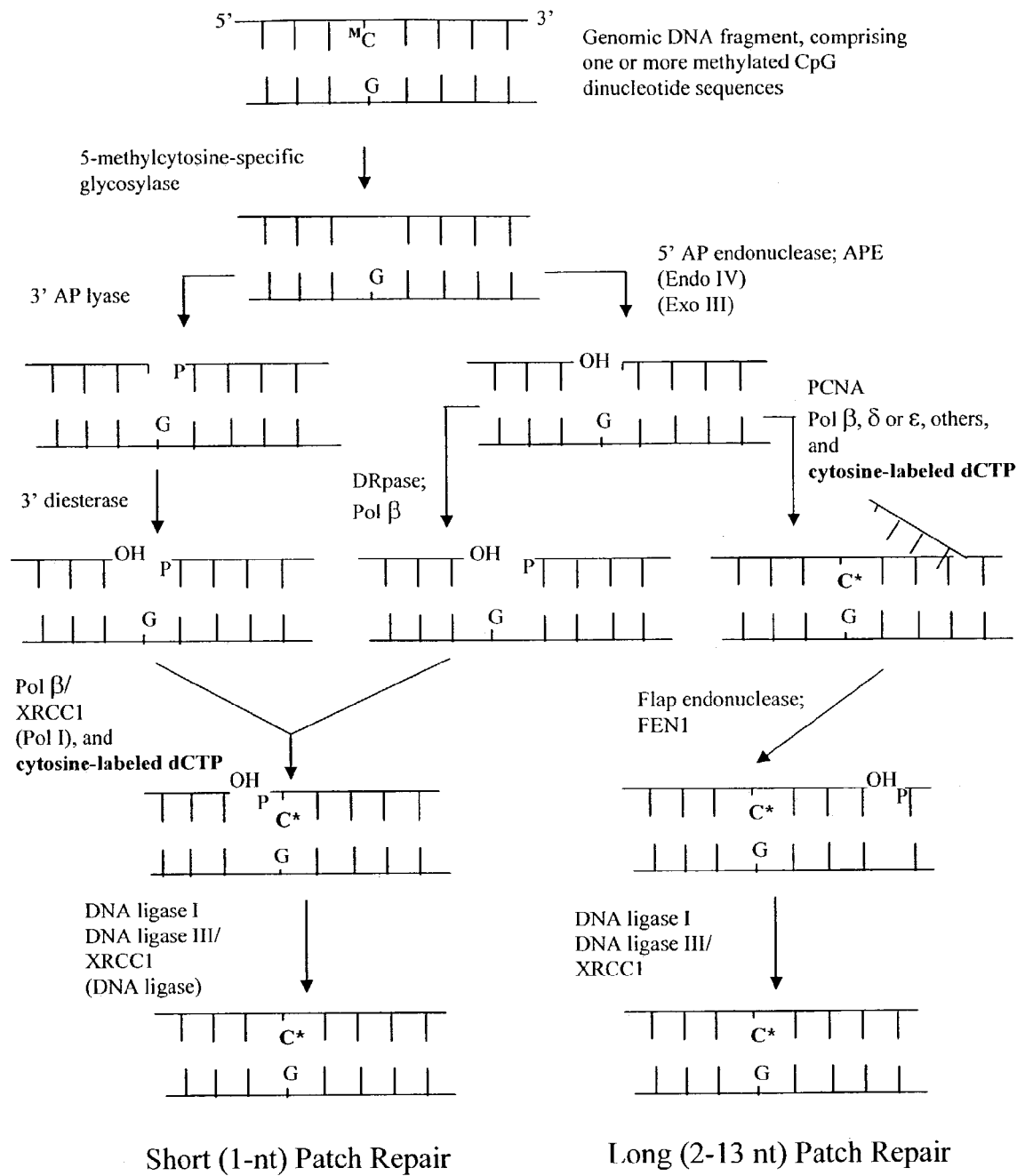
FIG. 1 illustrates how genomic DNA fragments comprising one or more methylated CpG dinucleotide sequences ("$^M$CpG")are specifically labeled at those sequences according to the present invention. Genomic DNA is digested with one or more restriction enzymes, and treated with 5-methycytosine deglycosylase (5-MCDG)to specifically remove methylcytosine bases ("$^M$C"). The treated abasic DNA is repaired using short-patch or long-patch (or both) base excision repair ("BER") enzymes in the presence of labeled dCTP to specifically label and identify methylated CpG residues in the genomic DNA sample. Essentially, the methylated cytosine bases of $^M$CpG dinucleotide sequences are replaced with labeled cytosine. Bacterial equivalents of particular mammalian BER enzymes are shown in parentheses.

Definitions:

The term "5-meythylcytosine deglycosylase," or "5-MCDG" refers to a DNA glycosylase activity that acts to cleave glycosylic bonds at methylated CpG sites of DNA, and remove 5-methylcytosine (5-MeC) from the DNA backbone, including but not limited to those mono- and bi-functional enzymes (e.g., MBD4 (G/T mismatch degylcosylase), and G/T mismatch-specific thymine-DNA glycosylase) described from human or chicken sources (Zhu et al., *Proc. Natl. Acad. Sci. USA* 98:5031-6, 2001; Zhu et al., *Nuc. Acid Res.* 28:4157-4165, 2000; and Neddermann et al., *J.B.C.* 271:12767-74, 1996; Vairapandi & Duker, *Oncogene* 13:933-938, 1996; Vairapandi et al., *J. Cell. Biochem.* 79:249-260, 2000), or the functional equivalents thereof, including functional deletion mutants thereof. For example, N-terminally deleted forms of human or avian MBD4 (G/T mismatch DNA glycosylases; which also have 5-methylcytosine deglycosylase activity) show enhanced 5-methylcytosine deglycosylase activity relative to the G/T mismatch deglycosylase activity (e.g., the ΔN273, ΔN378, and ΔN433 N-terminal deletion mutants described by Zhu et al., *Nuc. Acids Res.* 28:4157-4165, 2000), and are thus useful for purposes of the present invention. Preferably, the 5-methylcytosine deglycosylase enzymes are purified, partially purified, or recombinant. Preferably, the enzymes are recombinant.

The term "base excision repair," or "BER" refers herein to the method or process of repairing abasic sites within DNA resulting from removal of modified or damages base residues. Generally, the BER process is considered to include the removal of modified or damaged base residues.

The term "base excision repair enzymes," or "BER enzymes" refers herein to those combinations of enzymes or enzyme activities, that in addition to deglycosylases, are sufficient to complete base excision repair by at least one of short-patch or long-patch repair, via DNA backbone cleavage at apurinic or apyrimidinic (AP) sites, and may include but are not limited to AP endonuclease, AP lyase, DNA deoxyribophosphatase (dRPase), mammalian polymerase β (Pol β) 3'-diesterase (e.g., AP endonuclease), DNA ligase (e.g., I or III), Pol δ, Pol ε, structure-specific flap endonuclease ("FEN1"), and may include accessory components including, but not limited to proliferating cell nuclear antigen ("PCNA"; long-patch repair), replication factor-C ("RFC"; long-patch repair), scaffold XRCC1, nucleotide excision repair XPG proteins, replication protein A ("RP-A"), RNA (particularly CpG-rich RNA), ATP, RNA helicase, etc. The enzymes may be purified, partially purified, or recombinant. Preferably, the enzymes are recombinant.

The term "Observed/Expected Ratio" ("O/E Ratio") refers to the frequency of CpG dinucleotides within a particular DNA sequence, and corresponds to the [number of CpG sites/(number of C bases X number of G bases)] X band length for each fragment.

The term "CpG island" refers to a contiguous region of genomic DNA that satisfies the criteria of (1) having a frequency of CpG dinucleotides corresponding to an "Observed/Expected Ratio" >0.6, and (2) having a "GC Content" >0.5. CpG islands are typically, but not always, between about 0.2 to about 1 kb in length.

The term "methylation state" or "methylation status" refers to the presence or absence of 5-methylcytosine ("5-mCyt") at one or a plurality of CpG dinucleotides within a DNA sequence. Methylation states at one or more particular palindromic CpG methylation sites (each having two CpG CpG dinucleotide sequences) within a DNA sequence include "unmethylated," "fully-methylated" and "hemi-methylated."

The term "hemi-methylation" or "hemimethylation" refers to the methylation state of a palindromic CpG methylation site, where only a single cytosine in one of the two CpG dinucleotide sequences of the palindromic CpG methylation site is methylated (e.g., 5'-CC$^M$GG-3' (top strand): 3'-GGCC-5' (bottom strand)).

The term "hypermethylation" refers to the methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "de novo methylation" refers to the conversion of unmethylated post-synthesis CpG dinucleotide sequences (within a palindromic CpG methylation site) to fully methylated CpG sequences.

The term "maintenance methylation" refers to the conversion of post-synthesis hemimethylated CpG dinucleotide sequences (within a palindromic CpG methylation site) to fully methylated CpG sequences.

The term "microarray" refers broadly to both 'DNA microarrays,' and 'DNA chip(s),' as recognized in the art, encompasses all art-recognized solid supports, and encompasses all methods for affixing nucleic acid molecules thereto or synthesis of nucleic acids thereon.

The term "resolving" in relation to cytosine-labeled DNA fragments, refers to physical separation, at least in part, of the cytosine-labeled DNA fragments, and broadly encompasses art-recognized resolution methods, including but not limited to electrophoresis, RLGS, mass methods, microarray methods, differential binding methods, hybridization methods, and combination thereof.

The term "labeled dCTP" refers to dCTP that is labeled in the alpha phosphate position, cytosine base, or sugar moiety in a manner such that the derivative incorporated cytosine deoxyribonucleotide residue is thus labeled.

The term "labeled cytosine" refers to the derivative (from labeled dCTP) labeled incorporated cytosine deoxyribonucleotide residue.

The term "substantially identical," when used to define either a 5-methylcytosine deglycosylase or BER enzyme amino acid sequence, means that a particular subject sequence, for example, a mutant sequence, varies from the sequence of natural protein by one or more substitutions, deletions, or additions, the net effect of which is to retain at least some biological activity of the 5-methylcytosine deglycosylase or BER enzyme. Alternatively, DNA analog sequences are "substantially identical" to specific DNA sequences disclosed herein if: (a) the DNA analog sequence is derived from coding regions of the natural 5-methylcytosine deglycosylase gene; or (b) the DNA analog sequence is capable of hybridization of DNA sequences of (a) under moderately stringent conditions and which encode biologically active 5-methylcytosine deglycosylase; or (c) DNA sequences which are degenerative as a result of the genetic code to the DNA analog sequences defined in (a) or (b). Substantially identical analog proteins will generally be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Discovery and Diagnostic Methods Using 5-Methylcytosine Degylcosylase

Overview:

The present invention provides novel uses of 5-methylcytosine DNA glycosylase, in combination with art-recognized DNA repair enzymes, and in particular embodiments with DNA methyltransferase, to specifically label cytosine bases in methylated CpG dinucleotides in genomic DNA sequences. Such labeling occurs through enzymatic substitution of 5-methylcytosine with labeled cytosine, and allows, inter alia, for selection and cloning of sequences originally containing methylated CpG dinucleotides.

Particular embodiments of the present invention provide methods for identification of methylated, and/or potentially methylatable CpG dinucleotides in genomic DNA sequences. Sequences comprising such methylated, and/or potentially methylatable CpG dinucleotides may be cloned, sequenced, and/or mapped within the genome to provide useful methylation markers.

Additional embodiments provide methods for comparison of the methylation state of specific CpG dinucleotides, and of patterns thereof between normal and diseased genomic DNA samples.

Further embodiments provide methods for determining all potentially methylatable CpG dinucleotides in genomic DNA samples, or for differentially labeling existing $^M$CpG, and potentially methylatable CpG dinucleotide sequences in isolated or cellular genomic DNA.

Yet further embodiments provide methods for selectively isolating genomic DNA fragments corresponding to methylated CpG-containing genomic DNA fragments.

As will be obvious to those skilled in the relevant art, the present invention includes, but is not limited to the those embodiments disclosed herein below, which describe and teach particular preferred implementations of the invention in the context of various resolution and analytical methods, including RLGS, VGS and microarray hybridization.

Identification of Methylated CpG Sequences in Genomic DNA Using 5-Methylcytosine Deglycosylase According to particular embodiments of the present invention (see FIG. 1), a genomic DNA sample is isolated, digested with one or more restriction enzymes and treated with 5-methylcytosine DNA glycosylase to remove all methylcytosine bases within methylated CpG dinucleotide sequences. The treated abasic genomic DNA is repaired with DNA repair enzymes (e.g., base excision repair enzymes; "BER") in the presence of cytosine-labeled dCTP to specifically label and identify methylated CpG dinucleotides in the genomic DNA sample. Such labeled and identified fragments may be cloned and/or sequenced to provide useful methylation markers for comparative and diagnostic purposes.

Genomic DNA. Genomic DNA is purified from normal and/or diseased tissue samples using established, art-recognized methods. For example, genomic DNA is isolated from cells or tissue samples by the standard method of proteinase K digestion and phenol-chloroform extraction (Wolf et al., Am. J Hum. Genet. 51:478-485, 1992). Those skilled in the art will recognize that other techniques, such as those described in Maniatis et al. (Molecular Cloning: A Laboratory Manual, Cold Spring Harbor, N.Y., 1982) may be used for this purpose.

Restriction enzymes. Isolated genomic DNA is digested using one or more restriction endouncleases. Generally, restriction endonuclease digestion is useful, inter alia, to appropriately size the genomic DNA fragments to facilitate subsequent analysis and cloning. Those skilled in the art will recognize that a variety of enzymes can be employed to this end. Particular embodiments use but a single restriction enzyme, whereas others employ a plurality of restriction enzymes, used either individually (e.g., sequentially), or in combination (e.g., sequentially or contemporaneously). Preferably, a plurality of restriction enzymes are used. Preferably, at least one of the restriction enzyme(s) employed recognizes a 6-base cleavage motif cleavage (e.g., EcoRV; $5'GAT/ATC^{3'}$). Preferably, at least one of the restriction enzyme(s) employed recognizes a 4-base (e.g., MseI, $5'TT/AA^{3'}$), or 5-base (e.g., HinfI; $5'G/ANTC^{3'}$) cleavage motif. Preferably, at least one of the restriction enzyme(s) employed recognizes a 8-base (e.g., NotI; $5'GC/GGCCGC^{3'}$) cleavage motif. Preferably, if only one restriction enzyme is used, it recognizes a 4-base, or 5-base motif cleavage site. Preferably, the restriction enzyme(s) do not disrupt methylated CpG sequences. Preferably, the restriction enzyme(s) do not disrupt any CpG dinucleotide sequences, regardless of methylation status. Preferably, if the restriction enzyme cleavage sites do comprise CpG dinucleotides, they preferably produce 5'-extension-type staggered ends upon cleavage that can be repaired (filled in with, e.g., the Klenow fragment of DNA polymerase I) to retain the integrity of the corresponding genomic CpG methylation status (e.g., NotI; $5'GC/GGCCGC^{3'}$).

5-methylcytosine DNA glycosylase. The restricted genomic DNA is treated with 5-methylcytosine DNA glycosylase (5-MCDG) to specifically remove 5-methylcytosine bases (FIG. 1). Various art-recognized 5-MCDG enzymes, including those of human, chick embryo, murine myoblast (Zhu et al., 2000), and potentially of yeast origin, may be used for the inventive purpose, provided that they are, or can be made to be 5-methylcytosine specific in glycosidic bond cleavage. Additionally, N-terminally deleted forms of human or avian G/T mismatch DNA glycosylase (which also have 5-methylcytosine deglycosylase activity) show enhanced 5-methylcytosine deglycosylase activity relative to the G/T mismatch deglycosylase activity (e.g., the ΔN273, ΔN378, and ΔN433 N-terminal deletion mutants described by Zhu et al., Nuc. Acids Res. 28:4157-4165), and are thus useful for purposes of the present invention.

The human mono-functional version of 5-MCDG cleaves DNA specifically at fully methylated CpG sites, and is inactive on hemi-methylated DNA (Vairapandi & Duker, Oncogene 13:933-938, 1996; Vairapandi et al., J. Cell. Biochem. 79:249-260, 2000), whereas the chick enzyme prefers hemi-methylated DNA. Recombinant forms of human and chick embro 5-MCDGs have been produced that retain the substrate specificity of the respective naturally occurring enzymes in removing 5-MeC bases.

Other components, including but not limited to the proliferating cell nuclear antigen (PCNA), ATP, or an RNA component (e.g., CpG rich RNA), RNA helicase and/or synthetic oligoribonucleotides may be used to modulate or optimize particular 5-MCDG activity and/or specificity (Vairpandi et al., supra; Swisher et al., Nuc. Acid Res. 26:5573-5580, 1998). For example, human 5-MCDG activity may be associated with such accessory factors as the proliferating cell nuclear antigen (PCNA). Likewise, a recombinant version of chick embryo 5-MCDG has a greater activity for hemimethylated DNA than for fully methylated DNA, and its activity may be modulated by the addition of recombinant CpG-rich RNA, ATP and the enzyme RNA helicase (Zhu et al., Nuc. Acid Res. 28:4157-4165, 2000).

Preferably, genomic DNA is treated with mono-functional human or recombinant human 5-MCDG, which cleave glycosylic bonds specifically at fully methylated CpG sites of DNA, and are inactive on hemimethylated DNA (Vairapandi & Duker). Preferably, recombinant mono-functional human 5-MCDG is used. Preferably, such cleavage is specific to 5-methylcytosine residues. Preferably, the genomic DNA is digested with one or more restriction enzymes prior to 5-MCDG treatment.

Base excision repair (BER). In mammalian cells completion of base excision repair (BER) following DNA backbone cleavage at apurinic or apyrimidinic (AP) sites occurs by either short-patch BER, in which 1 nucleotide is replaced, or by long-patch BER, in which 2-13 nucleotides are replaced (see Memisoglu & Samson, Mutation Research 451:39-51, 2000, for a review).

According to the present invention, 5-MCDG treated genomic DNA, having apyrimidinic (AP) sites, is repaired via DNA backbone cleavage using purified or partially purified BER excision repair enzymes, or their recombinant and/or functional equivalents, in the presence of labeled dCTP to identify the genomic DNA positions containing 5-methylcytosine residues (FIG. 1).

Specifically, the DNA backbone is cleaved at apyrimidinic sites by an AP endonuclease (e.g., "APE"; also known as Ref-1, Hap-1 and Apex), resulting in the formation of a 3'-hydroxyl and a 5'-abasic sugar phosphate, deoxyribose phosphate (dRP) (FIG. 1). Alternatively, the AP site can be cleaved by an AP lyase activity, catalyzing the formation of a 5'-phosphate and 3'-fragmented deoxyribose (FIG. 1). Particular DNA glycosylases, as mentioned above, may either comprise or be associated with AP lyase activity.

In the short-patch pathway, the 5'-deoxyribophosphate (5'-dRP) terminus created by AP endonuclease is removed by the DNA deoxyribophosphatase ("dRPase") activity of mammalian polymerase (Pol β), and the 3'-abasic terminus left by the alternative use of AP lyase is removed by the "3'-diesterase" activity associated with AP endonucleases (FIG. 1). In both cases, the resulting abasic gap is repaired by incorporation therein of labeled cytosine ("C*") using Pol β in the presence of cytosine-labeled dCTP, and the remaining DNA strand break is sealed using, e.g., either DNA ligase I or DNA ligase III (FIG. 1).

These various components, or their recombinant and/or functional equivalents, are basic elements of the inventive short-patch BER process, but it will be obvious to those skilled in the art that certain accessory components such as the scaffold XRCC1 (Vidal et al. EMBO J. 20:6530-6539, 2001) and nucleotide excision repair XPG (Klungland et al. Mol. Cell. 3:33-42, 1999) proteins can be used to enhance DNA repair activity in certain situations, although they are not absolutely required (Klungland et al. Mol. Cell. 3:33-42, 1999; Kubota et al. EMBO J. 15:6662-6670, 1996).

In the long-patch BER inventive pathway, extension from the 3'-OH group left by AP endonuclease is achieved by using, e.g., either Pol δ or Pol ε, and involves displacing the strand containing the 5'-dRP for several nucleotides (FIG. 1) (see also Styuki et al Oncogene 20:835-843, 1998). The structure-specific flap endonuclease ("FEN1") is used to remove the resulting 'flap' structure to produce a DNA strand break that is ligated by DNA ligase as described above. In addition to DNA polymerase, FEN1 and DNA ligase, the long-patch BER pathway requires at least two accessory factors, namely proliferating cell nuclear antigen ("PCNA") and replication factor-C (RFC), which enhance the activity of DNA polymerase δ and ε (Styuki et al). Replication protein A (RP-A) may also be useful to enhance PCNA-dependent repair activity (Dianov et al. Biochemistry 38:11021-5, 1999).

The above-described BER processes are performed using purified enzymes, or partially-purified fractions of cellular extracts (e.g., such as those described by Vairapandi & Duker, Oncogene 13:933-938, 1996; Vairapandi et al., J. Cell. Biochem. 79:249-260, 2000; Dianov et al., Biochemistry 38:11021-5, 1999; Pascucci et al., J. Biol. Chem. 274:33696-702). Preferably, a purified or recombinant 5-MCDG is used in combination with purified, partially purified or recombinant BER enzymatic activities. Preferably a recombinant 5-MCDG is used in combination with purified, or recombinant BER enzymatic activities. In practicing the various embodiments of the present invention, a variety of art-recognized accessory factors, including but not limited to those discussed above, are or may be used in combination with the 5-MCDG and/or BER enzymes to enhance or modify activity or specificity.

Preferably, the BER repair is performed under the following conditions: 1× Buffer A (50 mM Tris-Cl (pH 8.8), 10 mM $MgCl_2$, 100 mM KCl, 1.0 mM DTT, 10% glycerol); 50 μM [$^{32}$P]-dCTP (or the functional equivalent of a non-radio label), 50 μM dGTP, 50 μM dTTP, 50 μM dATP; and 10 μg of restricted 5-methylcytosine deglycosylase-treated genomic DNA in a reaction volume of about 50 μl. Preferably, the BER reaction is for about 15 min at 37° C.

For purposes of the present invention, the BER treatment and the 5-methylcytosine deglycosylase treatment are optionally performed simultaneously.

The cytosine label optionally comprises radio-labels, fluorescent labels, phosphorescent labels, enzymic labels, mass labels detectable in a mass spectrometer, amplifiable labels (e.g., such as Biotin- and Fluorescein-labeled dCTP), and combinations thereof Preferably, amplifiable labels are used.

It will be obvious to those skilled in the art that functional equivalents of the above described 5-MCDG and BER enzymes can be used for the present invention, provided that the DNA deglycosylase is specific for 5-MeC, and preferably specific for fully-methylated CpG dinucleotide pairs. Additionally, such functional equivalents can be obtained from a variety of sources, including but not limited to human, chicken, mouse, yeast, and bacteria. Both Saccharomyces cerevisiae and Schizosaccharomyces pombe have homologues to mammalian FEN 1, PCNA and RFC (Memisoglu & Samson, Mutation Research 451:39-51, 2000).

Table I shows a summary of some art-recognized BER and DNA glycosylase enzymes and genes, including those of 5-MCDG, which are useful in practicing the present invention:

TABLE I

Summary of some base excision repair (BER) genes

| Enzyme | E. coli | S. cerevisiae | S. pombe | Human |
|---|---|---|---|---|
| DNA glycosylase | | | | |
| 5-Methylcytosine DNA glycosylase | | | | MBD4 TDG other |
| Uracil DNA glycosylase | ung | UNG1 | | UDG1 |
| 3MeA DNA glycosylase | alkA tag | MAG | mag1 mag2[b] | AAG[a] |
| 8-oxoguanine DNA glycosylase/AP lyase | fpg | OGG1[a] | | OGG1[a] |
| MutY G:A mismatch glycosylase/AP lyase | mutY | | | MYH |
| Thymine glycol DNA glycosylase/AP lyase | nth | NTG1/OGG2 NTG2 | ntg1 | NTG1 |
| TDG T:G mismatch DNA glycosylase | | | | TDG |
| AP endonuclease | | | | |
| Exonuclease III | xth | ETH1/APN2 | eth1[b] | APE/REF1/HAP1 |
| Endonuclease IV | nfo | APN1 | apn1[b] | |
| Additional factors | | | | |
| Flap endonuclease | | RTH1/RAD27 | rad2 | FEN1 |
| Proliferating cell nuclear antigen | | POL30 | pcn1 | PCNA |

TABLE I-continued

Summary of some base excision repair (BER) genes

| Enzyme | E. coli | S. cerevisiae | S. pombe | Human |
| --- | --- | --- | --- | --- |
| Replication Factor C | | RFC | rfc | RFC |
| XRCC1 | | | | XRCC1 |
| DNA polymerase | | POL IV | | Pol β |
| | | POL 3 | pol 3 | Pol δ |
| | | POL 2 | cdc20 | Pol ε |
| DNA ligase | ligA | CDC9 | cdc17 | LIG1, LIG3 |

[a]Gene product possess similar enzymatic activity to E. coli homologue, but the protein does not exhibit sequence similarity, thus the proteins are orthologs.
[b]Identified by database search, enzymatic activity has not been verified.

Selection of DNA fragments comprising one or more labeled CpG dinucleotide sequences. Standard, art-recognized methods are used to visualize and/or select DNA fragments comprising one or more labeled cytosine residues, corresponding to methylated genomic DNA sites.

For example, in particular embodiments at least one of: restriction landmark genome scanning (RLGS; e.g., Eng et al., *Nature Genetics* 25:101-102, 2000; Costello et al., *Nature Genetics* 25:132-138, 2000; Zhu et al., *Proc. Natl. Acad. Sci. USA* 96:8058-8063, 1999); or virtual genome scanning (VGS; e.g., Rouillard et al. *Genome Research* 11:1453-1459, 2001) is used to visualize and/or select DNA fragments comprising one or more labeled cytosine residues. In alternative high-throughput embodiments, microarray-based methods are used to visualize and/or select DNA fragments comprising one or more labeled cytosine residues (Yan et al., *Clin. Canc. Res.* 6:1432-1438, 2000).

For RLGS embodiments, genomic DNA is digested using one or more restriction endonucleases and labeled with labeled dCTP according to the present invention (FIG. 1), and the resulting specifically labeled DNA fragments are subjected to electrophoresis in a first-dimension agarose gel, followed by digestion in situ with an additional restriction enzyme (to further cleave the DNA fragments to facilitate resolution), and separation in a second-dimension acrylamide slab gel. The 2-dimensional gels are dried and imaged for determination of the labeling pattern. For example, dried gels are exposed to PHOSPHORIMAGER™ plates (Molecular Dynamics) for a sufficient period, and then scanned with a PHOSPHORIMAGER™ (e.g., at a resolution of about 176 microns per pixel) or exposed to autoradiographic film for analysis. Various software is optionally used for spot detection and quantification (e.g., VISAGE™ software; Bio-Image, Ann Arbor, Mich.). It is not required that a restriction endonuclease cleavage map, or sequence of the genomic DNA is known, but such information facilitates analyses as in the case of embodiments employing VGS (Rouillard et al., 2001).

Those skilled in art will recognize that a variety of labels can be used to practice the present invention. The cytosine label optionally comprises radio-labels, fluorescent labels, phosphorescent labels, enzymic labels, mass labels detectable in a mass spectrometer, amplifiable labels (e.g., such as Biotin- and Fluorescein-labeled dCTP), and combinations thereof. Preferably, amplifiable labels are used.

Those skilled in the art will also recognize that a variety of restriction enzymes can be employed for such RLGS and VGS embodiments. Particular embodiments use but a single restriction enzyme, whereas others employ a plurality of restriction enzymes, used either individually (e.g., sequentially), or in combination (e.g., sequentially or contemporaneously). Preferably, a plurality of restriction enzymes are used. Generally, restriction endonuclease digestion is useful to appropriately size the genomic DNA fragments to facilitate subsequent analysis and cloning. Preferably, at least one of the restriction enzyme(s) employed recognizes a 6-base or motif cleavage site (e.g., EcoRV; $^5$'GAT/ATC$^{3'}$). Preferably, at least one of the restriction enzyme(s) employed recognizes a 4-base (e.g., MseI, $^5$'TT/AA$^{3'}$), or 5-base (e.g., HinfI; $^5$'G/ANTC$^{3'}$) motif cleavage site. Preferably, at least one of the restriction enzyme(s) employed recognizes a 8-base (e.g., NotI; $^5$'GC/GGCCGC$^{3'}$) motif cleavage site. Preferably, if only one restriction enzyme is used, it recognizes a 4-base, or 5-base motif cleavage site. Preferably, the restriction enzyme(s) do not disrupt methylated CpG sequences. Preferably, the restriction enzyme(s) do not disrupt any CpG dinucleotide sequences, regardless of methylation status. Preferably, if the restriction enzyme cleavage sites do comprise CpG dinucleotides, they produce staggered ends upon cleavage that can be repaired to retain the integrity of the corresponding genomic CpG methylation status (e.g., NotI; $^5$'GC/GGCCGC$^{3'}$).

Figure 2:
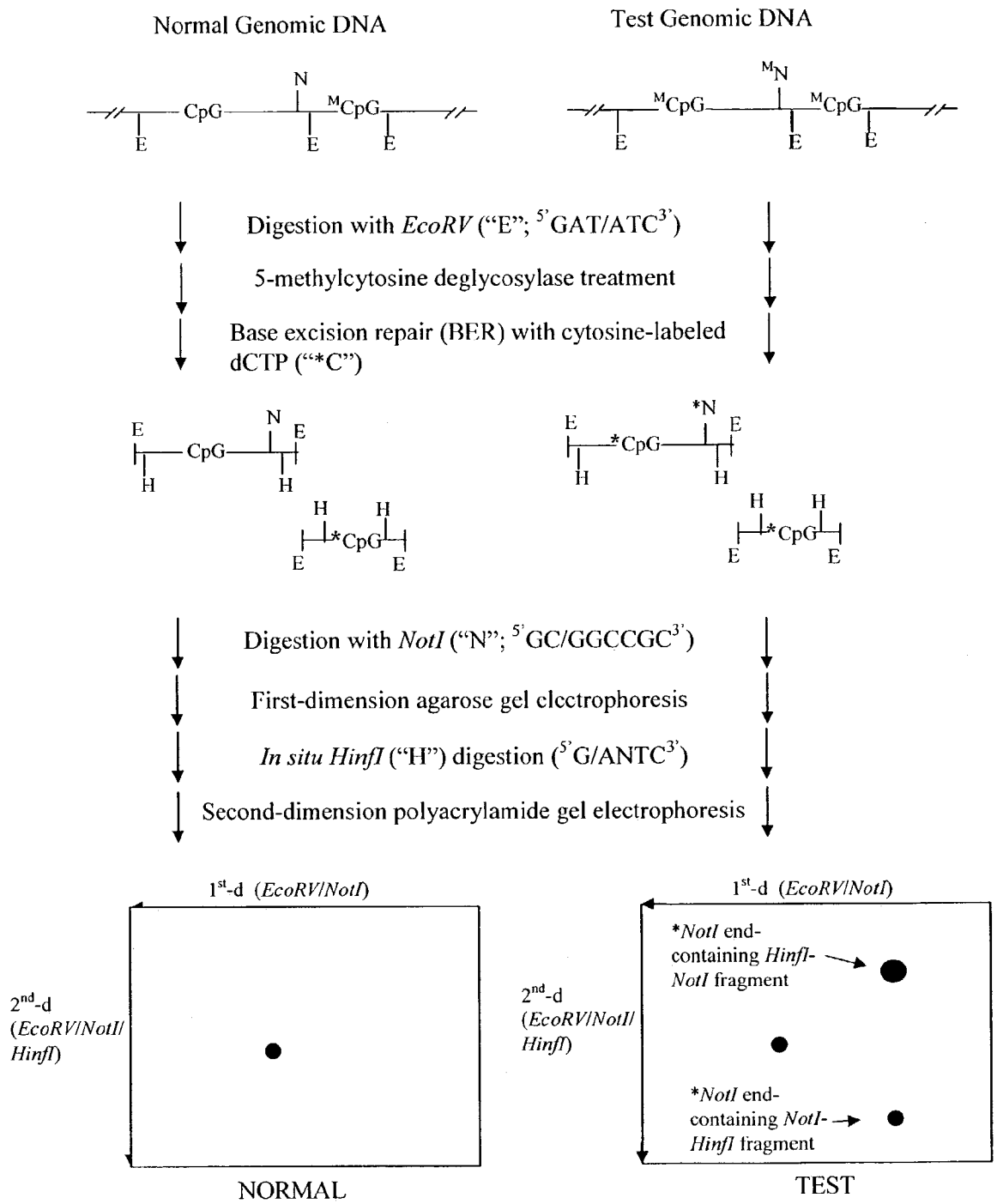
FIG. 2 illustrates a comparative restriction landmark genomic scanning (RLGS) embodiment of the present invention. Genomic DNA isolated from reference and test tissue is separately digested using one or more restriction endonucleases (here EcoRV; "E"), and specifically labeled with labeled dCTP using 5-MCDG and BER enzymes according to the method illustrated in FIG. 1. The resulting specifically-labeled DNA fragments are digested with an additional restriction endonuclease (here NotI; "N") and subjected to electrophoresis in a first-dimension agarose gel, followed by digestion in situ with an additional restriction endonuclease (here HinfI; "H"), and separation in a second-dimension acrylamide slab gel. The 2-dimensional gels are dried and imaged for determination of the labeling pattern. Labeled fragments that appear as spots on the imaged 2-dimensional gels correspond to genomic sequences comprising $^M$CpG dinucleotide sequences. The inventive methods are not limited to any particular restriction endonucleases or combination thereof.

FIG. 2 illustrates a comparison of the methylation patterns between "Normal" and "Test" genomic DNA samples, according to a preferred RLGS embodiment of the present invention employing a combination of three restriction enzymes (NotI, EcoRV and HinfI) that are routinely employed in prior art RLGS analyses. Here, the test genomic sample (upper-right side of FIG. 2) contains three $^M$CpG sequences (one within a NotI cleavage site; "*N"), two of which (including that of the NotI cleavage site; "*N") correspond to positions that are not methylated at the corresponding normal genomic DNA positions (upper-left portion of FIG. 2). The normal and test genomic DNA samples are separately digested with EcoRV ("E"; $^5$'GAT/ATC$^{3'}$), treated with 5-methycytosine deglycoslyase, and subjected to base excision repair (BER) in the presence of cytosine-labeled dCTP ("*C") to specifically label methylated CpG sequences present in the respective genomic DNA samples (see upper portion of FIG. 2). Essentially, the methylated cytosine of $^M$CpG sequences is replaced by labeled cytosine ("*C"; to produce "*CpG") (see middle of FIG. 2).

The respective cytosine-labeled genomic DNA fragments are further digested with NotI ("N"; $^5$'GC/GGCCGC$^{3'}$), subjected to first-dimension electrophoresis through agarose (e.g., 0.8% tube gels, 60 cm in length), and digested in situ using HinfI ("H"; 5'G/ANTC$^{3'}$). The HinfI-digested DNA in the respective agarose tube gels are subjected to electrophoresis in a second dimension through respective non-denaturing polyacrylamide gel (e.g., 5%; rotated 90° relative to the direction of electrophoresis of the tube gel, and joined at the top to the perpendicular tube gel by molten agarose).

The resulting respective 2-dimensional gels are dried and imaged for determination of the labeling patterns (see bottom of FIG. 2).

FIG. 2 (see bottom 2-dimensional gels) illustrates that genomic DNA fragments comprising one or more methylated CpG sequences, and patterns thereof, are detectable as corresponding labeled spots in 2-dimensional gel images. The positive occurrence of a methylated CpG sequence ($^{M}$CpG) in a particular test genomic DNA fragment, but not in the respective normal genomic DNA fragment, results in the appearance of a new spot, a brighter spot (in the case where the respective fragments share other $^{M}$CpG sequences in common), or both (e.g., see the new and brighter spot in the right-hand 2-dimensional gel of FIG. 2) in the 2-dimensional spot pattern of the test sample gel.

Generally speaking, intensity among imaged 'spots' varies depending upon several factors, including the relative number of labeled cytosine residues (i.e., $^{M}$CpG dinucleotides) per treated DNA fragment, potential positional overlap of unresolved or partially resolved fragments, relative 'copy number' (e.g., deviation from typical diploid number), polymorphism, and correspondence with sex chromosomes. Typically and primarily, however, the relative intensity among imaged 'spots' varies according to the relative number of labeled cytosine residues (corresponding to genomic $^{M}$CpG dinucleotide sequences) per spot.

As stated above, the cytosine label optionally comprises radio-labels, fluorescent labels, phosphorescent labels, enzymic labels, mass labels detectable in a mass spectrometer, amplifiable labels (e.g., such as Biotin- and Fluorescein-labeled dCTP), and combinations thereof. Preferably, amplifiable labels are used.

Figure 3:
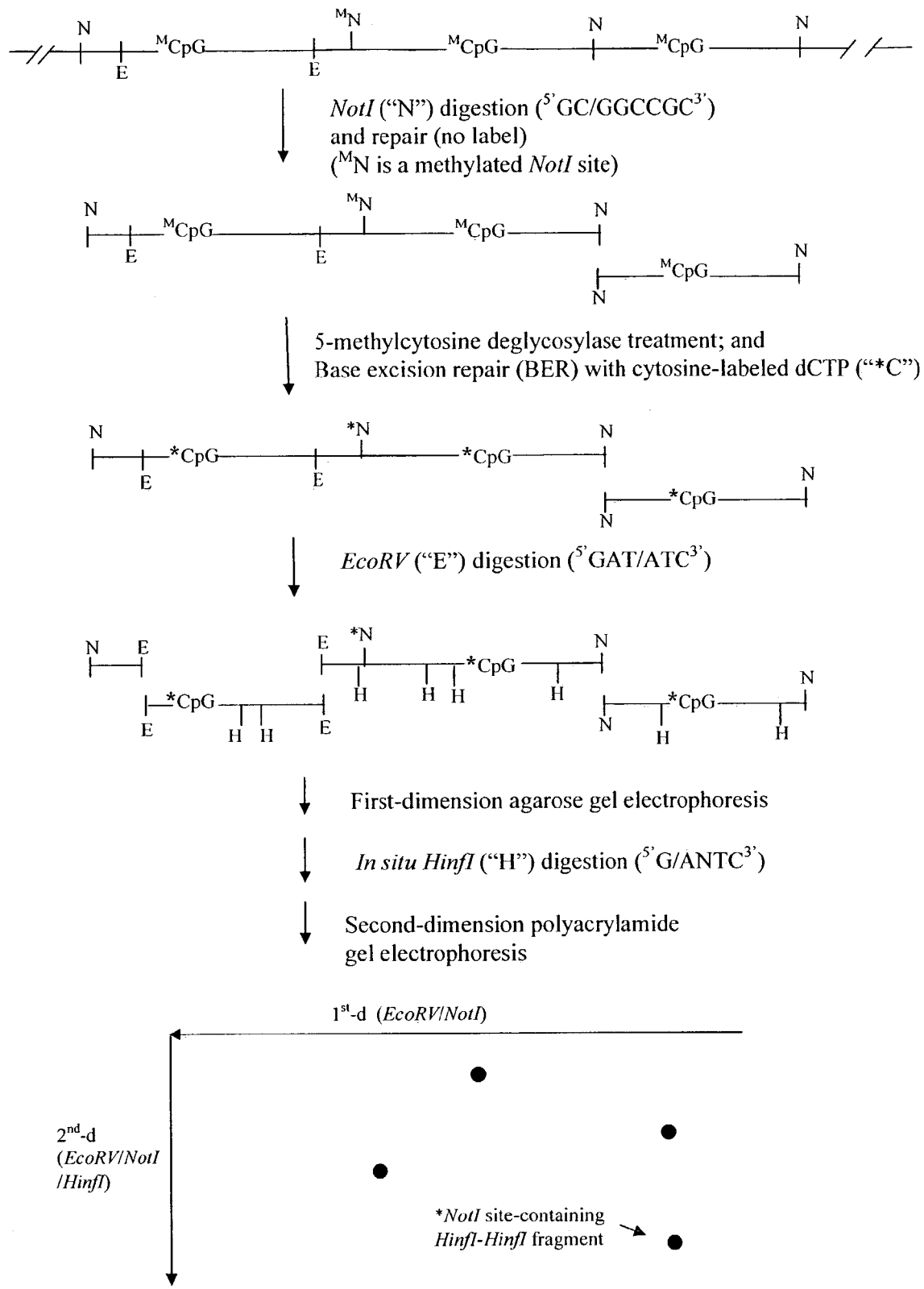
FIG. 3 illustrates an inventive embodiment similar to that shown in FIG. 2, except that the order of restriction digestion has been reversed (here NotI, followed by EcoRV). The inventive methods are not limited to any particular restriction endonucleases or combination thereof, and are not limited by any particular ordering of endonuclease digestion. Treatment of only a single genomic DNA sample is shown, but as in the embodiment of FIG. 2, comparisons between or among a plurality of genomic DNA samples are encompassed by the inventive methods.

FIG. 3 illustrates an alternate RLGS embodiment of the present invention that uses the same set of three restriction endonucleases (NotI, EcoRV and HinfI), but (in contrast to the embodiment of FIG. 2) digestion with the methylation-sensitive restriction endonuclease NotI occurs prior to 5-methylcytosine deglycosylase and BER treatments so that methylated NotI sites are not cleaved. Accordingly, genomic DNA is cleaved with NotI ("N"; 5'GC/GGCCGC$^{3'}$), and the resulting staggered ends are repaired (e.g., with T4 DNA polymerase, or SEQUENASE™ version 2.0, U.S.B.) using unlabeled deoxynucleotides (in contrast to prior art RLGS procedures, which introduce labeled nucleotides when repairing staggered NotI ends).

The NotI-restricted and repaired DNA is labeled at positions corresponding to methylated CpG dinucleotide sequences ("$^{M}$CpG"), including those within NotI sites, by treating with 5-methyldeglycosylase and subjected to BER using labeled dCTP ("*C"; FIG. 3). The NotI-restricted, labeled DNA is further digested with EcoRV ("E"; 5'GAT/ATC$^{3'}$) to facilitate further separation and analysis, and subjected to electrophoresis in a first dimension through an agarose tube gel.

DNA fragments in the first dimension agarose gel, as in the embodiment of FIG. 2, are digested in situ using HinfI ("H"; 5'G/ANTC$^{3'}$), and subjected to electrophoresis in a second dimension through a polyacrylamide gel. The resulting 2-dimensional gel is dried and imaged for determination of the labeling pattern (bottom of FIG. 3). As in the embodiment of FIG. 2, the relative intensity among imaged 'spots' primarily varies according to the relative number of labeled cytosine residues (corresponding to genomic $^{M}$CpG dinucleotide sequences) per DNA fragment (spot). As in the embodiment of FIG. 2, this embodiment can be used to compare the methylation status of CpG residues between normal and test genomic DNA samples, or between or among a reference spot pattern and one or more test patterns.

In a variant of the embodiment of FIG. 3, the sample is split into two portions at the step of DNA digestion by EcoRV. One portion is digested with EcoRV, and processed as in FIG. 3, whereas the other portion is digested with EcoRV plus NotI, and processed as in FIG. 3. The second NotI digestion in this variation serves to cleave those NotI sites that were uncleavable by virtue of their methylation status in the genomic DNA, but that were subsequently rendered cleavable by virtue of the inventive treatments with 5-methylcytosine deglycosylase and base excision repair (BER). The 2-dimensional gel images corresponding to the NotI/EcoRV/HinfI combination, and the NotI/EcoRV/NotI/HinfI combination are then compared. The presence, in the NotI/EcoRV/HinfI combination 2-dimensional gel image, of any spots corresponding to genomic fragments comprising internal NotI-associated $^{M}$CpG sequences, is indicated by the NotI-dependent conversion of such a spot into at least two new spots in the NotI/EcoRV/NotI/HinfI combination 2-dimensional gel. For example, In this variant, the 2-dimensional spot corresponding to the NotI-containing HinfI-HinfI fragment in the NotI/EcoRV/HinfI 2-dimensional gel of FIG. 3 would be absent from the corresponding NotI/EcoRV/NotI/HinfI combination 2-dimensional gel, and two new smaller labeled fragments would be detectable.

While those skilled in the art will recognize that a variety of restriction enzymes (alone and in combination, and in various orders), can be employed for RLGS embodiments of the present invention, use of the particular combination of NotI, EcoRV and HinfI (as in FIGS. 2 and 3) offers several advantages, and is thus preferred in particular applications, especially those where particular selected fragments (spots) are to be cloned.

One advantage of using the particular combination of NotI, EcoRV and HinfI is that the methylation-sensitive restriction endonuclease NotI is known to specifically cleave DNA at CpG islands (i.e, unmethylated positions thereof), and has been routinely employed along with EcoRV and HinfI to differentially compare the methylation status of normal and test genomic DNA samples using RLGS (Eng et al., *Nature Genetics* 25:101-102, 2000; Costello et al., *Nature Genetics* 25:132-138, 2000). Thus, the 2-dimensional position/pattern, and in some cases genetic linkage, of many end-labeled (i.e, NotI repaired ends) NotI/EcoRV/HinfI fragments are known in the art, and this information can be used to compliment the present invention by helping to determine the nature (e.g., CpG island or non-CpG island) and linkage of particular spots on the inventive 2-dimensional gels.

An additional advantage (see below, under "Cloning, sequencing and mapping . . . "), of using the particular combination of NotI, EcoRV and HinfI is that existing prior art genomic libraries (e.g., 'boundary' libraries), such as arrayed human genomic libraries of NotI/EcoRV fragments can be used to rapidly obtain cloned DNA corresponding to particular fragments (spots) of interest.

Significantly, however, the present invention is not limited by the availability of any particular boundary library. This is because the present inventive methods to not depend on NotI end-labeling, and rather provide for methylation-specific *CpG labeling and detection of, DNA fragments that would not be detectable by prior art RLGS methods (e.g., EcoRV-EcoRV, EcoRV-HinfI, or HinfI-HinfI fragments). Thus, the benefits of virtual genome scanning (VGS) methods can be fully realized, because cytosine-labeled EcoRV-EcoRV, EcoRV-HinfI, or HinfI-HinfI fragments (i.e., positive spots) that would otherwise correspond to 'holes' in the prior art NotI/EcoRV boundary libraries can nonetheless be correlated and characterized by virtue of the corresponding virtual DNA fragment sequences.

Therefore, a great variety of restriction enzyme combinations are useful in practicing the present invention, despite the absence of existing NotI-based boundary libraries.

Additionally and significantly, DNA methylation analysis by the present invention is not limited to CpG-rich or CpG-island regions, and is not dependent upon methylation-sensitive digestion (differential digestion) by restriction enzymes that have CpG dinucleotides within or overlapping their recognition cleavage motifs.

Cloning, sequencing and mapping/identification of selected DNA fragments. Standard, art-recognized recombinant DNA techniques are used to clone and sequence selected DNA fragments. For example, selected DNA fragments corresponding to genomic fragments comprising one or more methylated CpG residues are cloned from preparative electrophoresis gels, using, for example PCR-mediated methods (Suzuki, H. et al., *DNA Res.* 1:245-250, 1994).

Alternatively, fragments ('spots') of interest are cloned indirectly using "boundary" libraries (Plass, C. et al., *DNA Res.* 4:253-255, 1997; Smiraglia, D. et al., *Genomics* 58:254-262, 1999). As mentioned above, prior art arrayed human genomic NotI/EcoRV boundary libraries can be used to quickly obtain cloned DNA corresponding to particular spots of interest. Such arrayed libraries contain the same subset of genomic fragments as those giving rise to the fragments displayed on NotI/EcoRV/HinfI RGLS profiles, and the exact plate, row and column positions of NotI/EcoRV clones in the array have been, or can readily be, matched to individual NotI/EcoRV/HinfI fragments in RLGS profiles.

For example, when clones from a single plate (of a NotI/EcoRV boundary fragment library comprised of 32 microtitre plates) are pooled and mixed with genomic DNA, the resultant RLGS gel is a normal profile with a defined set of spots showing enhanced intensity for that particular plate. This can be performed on all 32 plates of the library, and as well on their pooled rows and columns to map individual spots to exact three variable designations (e.g., plate, row and column addresses) in the library thereby providing immediate access to these clones and enabling uniform comparisons between different samples and laboratories, based on "three variable designations (Smiraglia, D. et al., supra; Costello et al., supra).

Such NotI/EcoRV fragment libraries, as described above, have 'holes,' in that they have been constructed to substantially preclude EcoRV-EcoRV fragments. Such holes are not of great concern for prior art RLGS applications, because such fragments are not labeled by NotI end-labeling, and are thus invisible in prior art RLGS images. The present inventive method, however, allows detection of all fragments comprising methylated CpG sequences, including those that do not comprise NotI sites and those that are not part of CpG islands (those contained in, e.g., EcoRV-HinfI, EcoRV-EcoRV, or HinfI-EcoRV fragments). Thus, for the present inventive methods, additional arrayed libraries are constructed and used in analogy with the arrayed NotI/EcoRV boundary fragment libraries of the prior art.

Additionally, as discussed above, VGS is used to provide sequence information (virtual cloning) for imaged cytosine-labeled DNA fragments, and the corresponding fragments can be cloned using VGS-based probes.

Generally, the selected fragments are characterized by evaluating them in view of genomic sequence information and genetic linkage maps.

Such RLGS and/or VGS embodiments are useful for identification of methylated CpG dinucleotide sequences in genomic DNA, or for comparison of the status, extent or pattern of CpG methylation between or among reference and test samples.

Comparison of methylation patterns. Comparisons of methylation patterns between or among normal and diseased tissues, or between a reference pattern and one or more test patterns, are within the scope of the present invention. Such comparisons are made, for example, by gel electrophoresis or RLGS (as illustrated in the embodiments of FIGS. 2 and 3 above). Alternatively, microarrays (described in detail below) are used to determine the status, relative levels, or patterns of methylated vs. unmethylated cytosines at particular genomic positions.

The present invention affords several advantages over prior art RLGS methods for comparison between or among methylation patterns, including but not limited to the following:

First, prior art RLGS detection of CpG methylation is limited by the use of only particular methylation-sensitive restriction enzymes, which effectively limits analyses to a corresponding number of CpG sequences within CG-rich or CpG island regions. By contrast, the present invention allows detection of all methylated and differentially methylated CpG sequences, including those that are neither associated with NotI sites, nor with NotI site-containing CpG islands (NotI cuts predominantly, but not exclusively at CpG islands). Such fragments would go undetected by prior art methods based on fragment labeling by repair of, for example, NotI staggered ends. Any DNA fragment comprising a $^M$CpG sequence, but unlabeled by virtue of not having a cleaved NotI terminus, for example, would be invisible in prior art methods (e.g., the 2-dimensional spot corresponding to the NotI-containing HinfI-HinfI fragment in the 2-dimensional gel of FIG. 3 could not be analyzed by prior art methods).

Second, prior art RLGS detection of CpG methylation is limited by dependence (for detection) upon end-labeling of DNA fragment termini. By contrast, the present invention specifically labels only genomic fragments that comprise one or more methylated CpG sequences, and not as in the case of prior art methods, all DNA fragments that have a NotI staggered end, and that may or may not comprise methylated CpG sequences unrelated to those present in NotI cleavage sites. Thus, the inventive 2-dimensional gel patterns are not cluttered by labeled spots corresponding to those NotI sites that are unmethylated in both normal and test genomic DNA samples (i.e., largely corresponding to CpG islands with unchanged methylation status). Moreover, prior art artifacts related to artifactual labeling of sheared ends of genomic DNA are also avoided.

Third, prior art RLGS detection of CpG methylation is based upon the disappearance of (more accurately, the absence of) a test DNA spot (i.e., where a particular NotI site in a test DNA sample is methylated and therefore not cleaved by NotI digestion) relative to a corresponding spot present in the normal (test) DNA 2-dimensional pattern. By contrast, the present invention does not depend upon disappearance (absence) of a test DNA spot, but rather on the appearance (presence) of a test DNA spot not present (or present in a reduced intensity) in the corresponding reference pattern from normal genomic DNA. This distinguishing aspect has the advantage of avoiding particular prior art artifacts, such as failing to distinguishing methylation from differential deletion of particular DNA in the respective test genomic sample.

Use of 5-Methylcytosine Deglycosylase in Combination with DNA Methyltransferase

Further embodiments of the present invention are useful to analyze all potentially methylatable CpG dinucleotide sequences in a DNA sample. Such embodiments involve the use of one or more art-recognized DNA methytransferases in combination with the present inventive $^{M}$CpG-labeling with 5-methylcytosine deglycosylase.

DNA Amplification:

Particular hypermethylation embodiments afford enhanced sensitivity for methylation analysis, because the DNA is amplified by PCR prior to methylation analysis.

Amplification of Genomic DNA. A purified genomic DNA sample is amplified using amplification primers Preferably, the genomic DNA sample is first digested with one or more restriction enzymes as described herein above. Preferably, amplification is by polymerase chain reaction ("PCR"). Preferably, the primers are specific or arbitrary (in the sense of art-recognized arbitrarily primed PCR methods as described herein above, under "Background"). Preferably, the primers are specific to linkers ligated to the genomic DNA fragments. Alternatively, the amplification primers are preferably specific to the DNA sought to be amplified, or are designed to bias amplification to particular genomic regions, such as CpG-rich regions or CpG-island regions.

Hypermethylation of genomic DNA. The amplified genomic DNA or genomic DNA fragments are hypermethylated using DNA methyltransferase. Preferably, the methylase is a de novo methylase, or has de novo methylase activity. Preferably, the DNA methyltransferase is at least one of: Dnmt1 (mammalian methylase with a preference for hemimethylated CpG pairs); Dnmt3a (mammalian methylase with equal activity in vitro for unmethylated and hemimethylated DNA); Dnm3b (mammalian methylase with equal activity in vitro for unmethylated and hemimethylated DNA), or a non-mammalian DNA methylase.

Preferably, the non-mammalian DNA methylase is that of the cytosine DNA methylase from the wall-less prokaryote, Spiroplasma strain MQ1 (M.SssI) that methylates completely and exclusively CpG-containing sequences, including de novo methylation, and thus shows sequence specificity similar to that of mammalian DNA methylases. M.SssI methylates duplex DNA processively as judged by kinetic analysis of methylated intermediates, whereas the cytosine DNA methylases, M.HpaII and M.HhaI, from other prokaryotic organisms, appear to methylate in a non-processive manner or with a very low degree of processivity. SssI methylase has been shown to methylate duplex DNA completely (i.e., at all or nearly all CpG sequences) and processively, proceeding along a CpG containing substrate methylating one strand of DNA at a time (Renbaum & Razin, *FEBS LETT* 313:243-247, 1992). The M.SssI gene has been cloned (Renbaum et al., *Nucleic Acids Res.*, 18:1145-1152, 1990), and expression of the recombinant gene in host cells has enabled purification of active M.SssI protein (U.S. Pat. No. 5,296,371, to Razin et al., filed Oct. 4, 1991 and entitled DNA ENCODING SPIROPLASMA SP. DNA METHYLASE, incorporated by reference herein in its entirety).

In addition to M.SssI methylase and its respective gene, the use of other non-mammalian methylases and their respective genes, is contemplated and encompassed within the scope of the present invention. These include, but are not limited to the following: the hgiDIIM gene, encoding the methyltransferase (MTase) of the SaII isoschizomeric restriction-modification (R-M) system, HgiDII (GTCGAC) (Dusterhoft & Kroger, *Gene* 106:87-92, 1991); the gene encoding the DNA methyltransferase M.CviRI from Chlorella virus XZ-6E (Stefan et al., *Nucleic Acids Res.* 19:307-11, 1991); the gene encoding the XorII methyltransferase (M.XorII) from *Xanthomonas oryzae* pv. Oryzae (Choi & Leach, Mol. Gen. Genet. 24:383-90, 1994); and the HhaI methylase that has de novo methylase activity (Wu J. et al., *Cancer Res.* 56:616-622, 1996).

Treatment of hypermethylated DNA with 5-methycytosine deglycoslyase and BER. The amplified, hypermethylated DNA sample is treated, as described in detail herein above and as illustrated in FIGS. 1 and 2, with 5-methycytosine deglycoslyase, and subjected to base excision repair (BER) in the presence of labeled dCTP ("*C") to specifically label all methylated CpG dinucleotide sequences. The dCTP label optionally comprises radio-labels, fluorescent labels, phosphorescent labels, enzymic labels, mass labels detectable in a mass spectrometer, amplifiable labels (e.g., such as Biotin- and Fluorescein-labeled dCTP), and combinations thereof. Preferably, amplifiable labels are used.

Analysis of hypermethylation is completed using gel electrophoresis (RLGS, VGS), visualization of labeling, and excision of bands followed by sequencing, by cloning and sequencing of excised bands, or indirectly using boundary libraries, as described herein above.

Alternatively, complementary binding (e.g., hybridization)-based methods, such as microarrays are used to assess areas of hypermethylation.

Methylation pattern comparisons. Hypermethylation embodiments employing DNA methyltransferase in combination with 5-methylcytosine deglycosylase for comparisons of methylation patterns between or among normal and diseased tissues, or between a reference pattern and one or more test patterns or tissues, are within the scope of the present invention, using amplifiable labels in place of DNA amplification (see below). Such comparisons are made, for example, by gel electrophoresis, or RLGS (VGS) (as illustrated in the embodiments of FIGS. 2 and 3 above). Alternatively, complementary binding (e.g., hybridization)-based assays, such as microarrays (described below) are used to determine the relative levels or patterns of methylated vs. unmethylated cytosine bases at particular genomic positions.

Use of Amplifiable Labels to Distinguish Existing $^{M}$CpG Sequences from Potentially-Methylatable CpG Sequences. In alternate preferred hypermethylation embodiments, the potentially-methylatable CpG sequences in a genomic DNA sample are distinguished, at the level of cytosine labeling, from the methylated CpG ($^{M}$CpG) sequences already present in the isolated genomic DNA.

In these embodiments, the isolated, restricted genomic DNA is treated with 5-methylcytosine deglycosylase and subjected to BER repair in the presence of labeled cytosine to effectively replace $^{M}$CpG sequences with labeled CpG sequences (*CpG). The amplifiable label is chosen to preclude transfer, by DNA methyltransferases, of the methyl group from S-adenosylmethionine to the 5'-position of the pyrimidine (cytosine) ring. For example, Biotin-labeled dCTP is used. The $^{Biotin}$C-labeled genomic DNA fragments are then hypermethylated using DNA methyltransferase as described above, whereby CpG sequences, but not $^{Biotin}$CpG sequences, are methylated. The hypermethylated, $^{Biotin}$CpG-labeled genomic DNA fragments are then treated with 5-methylcytosine deglycosylase and subjected to BER repair in the presence of Fluorescein-labeled dCTP to replace $^{M}$CpG sequences with Fluorescein-labeled CpG sequences ($^{Fl}$CpG). In this manner, $^{M}$CpG sequences already present in the isolated genomic DNA fragments are Biotin-labeled, whereas subsequently hypermethylated $^{M}$CpG sequences are Fluorescein-labeled. There is no need to amplify the fragments themselves, as in the above-described hypermethylation embodiment, because efficient detection is facilitated by the amplifiable labels.

The Biotin- and Fluorescein-labeled genomic DNA fragments are then resolved, for example, using RLGS or microarrays and detected based on the presence of the distinguishable labels as described in detail herein below (e.g., according to a Tyramide Signal Amplification "TSA™ protocol involving either sequential exposure to strepavidin-HRP, and anti-Fluorescein-HRP, or independent exposure to strepavidin-HRP, or anti-Fluorescein-HRP), whereby a comparison (either within a genomic DNA sample, or between or among genomic DNA samples) of the existing CpG methylation status, extent, or pattern with the potentially-methylatable CpG methylation status, extent, or pattern is enabled.

Hypermethylation of Cellular DNA. Preferably, hypermethylation is affected at the level of isolated genomic DNA as described above. In this case, comparisons between or among isolated genomic DNA samples are useful to compare the status, extent or pattern of existing CpG methylation, the status, extent or pattern of potentially methylatable CpG residues, or both. The degree of CpG hypermethylation (potential methylation) affected by DNA methyltransferase is inversely proportional to the extent of existing CpG methylation.

Alternatively, however, hypermethylation is affected at the cellular level, where cells of interest are transiently transfected with an expression vector directing over-expression of a methyltransferase, such as at least one of: Dnmt1; Dnmt3a; Dnm3b; M.SssI methylase; and HhaI methylase. Preferably, such expression is accomplished using art-recognized expression vectors. Preferably, relatively methylation insensitive promoters, such as SV40 early and CMV promoters that contain no HhaI sites, are employed to drive methylase expression from such expression vectors.

According to the present invention, the pattern of potentially methylatable CpG residues in isolated genomic DNA samples differs from the pattern in the corresponding transiently transfected cell, due to a variety of physiological factors, including but not limited to cellular differentiation state, and transformation state. Accordingly, affecting hypermethylation at the cellular level, followed by isolation of genomic DNA and cytosine labeling according to the above-described embodiments allows for the cellular determination (or the relative determination between or among cells or tissues) of those CpG residues that are potentially methylatable in the context of particular cellular physiology.

High-throughput Microarray Embodiments

Alternative high-throughput embodiments are encompassed within the scope of the present invention. For example, microarray-based methods are useful to visualize and/or select DNA fragments comprising one or more labeled cytosine residues. Microarray-based methods, involving hybridization of labeled nucleic acid molecules to indexed arrays of specific nucleic acid sequences on solid supports are widely recognized in the art (see e.g., Yan et al., *Clin. Canc. Res.* 6:1432-1438, 2000).

The screening arrays of the present invention comprise a plurality of nucleic acid molecules affixed to a solid support or chip. These affixed nucleic acid molecules function as known probes for detecting the identity/abundance of targets by virtue of complimentary binding (hybridization). Affixed nucleic acid molecules include, but are not limited to, cDNA molecules, amplified genomic DNA fragments, cloned DNA fragments, and oligonucleotides synthesized in situ (on the chip) or immobilized on the chip after synthesis. Preferably, the solid supports are of glass or nylon.

Preferably, the affixed nucleic acid molecules comprise CpG-rich sequences, although they may comprise sequences comprising but a single CpG dinucleotide sequence, or comprising but a few CpG dinucleotide sequences. Preferably, the affixed nucleic acid molecules comprise sequences derived from a genomic library or a genomic library enriched for CpG-rich sequences, such as the CGI library, the avian CGI library, or the mouse CGI library (available from the United Kingdom Human Genome Center). Preferably, the libraries do not contain repetitive sequences, which can be removed during library construction or prescreening by art-recognized methods, such as Cot-1 hybridization. In preferred embodiments the affixed nucleic acid molecules are themselves CpG island fragments. In preferred embodiments, the affixed nucleic acid molecules are CpG islands comprising expressed sequences. In preferred embodiments, the affixed nucleic acid sequences comprise expressed sequences that are neither part of, or closely associated with CpG islands. In preferred embodiments the affixed nucleic acid molecules comprise differential methylation marker sequences that are diagnostically and/or prognostically associated with disease or cancer.

Nucleic acids are affixed to solid supports using one or more art-recognized methods, including but not limited to UV light, poly-L-lysine treatment and heat, or are synthesized in situ (on the chip). Preferably, at least about 100 nucleic acid sequences are affixed in the array, more preferably at least about 500 nucleic acid sequences are affixed, and even more preferably at least about 1000 nucleic acid sequences are affixed in the array.

Targets, corresponding to genomic DNA fragments treated according to the present invention, are hybridized with the affixed nucleic acid molecules of the arrays to determine methylation status/abundance and/or methylation pattern of the cytosine-labeled genomic DNA fragments, or to determine the differential methylation status/abundance or pattern between or among reference and test genomic DNA samples.

Specifically, genomic DNA samples are treated with 5-methycytosine deglycosylase, and subjected to base excision repair (BER) in the presence of labeled dCTP ("*C") to specifically label methylated CpG sequences (e.g., as illustrated in FIGS. 1 and 2). The cytosine label optionally comprises radio-labels, fluorescent labels, phosphorescent labels, enzymic labels, mass labels detectable in a mass spectrometer, amplifiable labels (e.g., such as Biotin- and Fluorescein-labeled dCTP), and combinations thereof. Preferably, amplifiable labels are used to enhance sensitivity.

The cytosine labeled DNA target fragments are then screened by hybridization using arrayed nucleic acid molecules (probes). Comparative analysis between or among genomic DNA samples is made by sequential and/or parallel screens.

The sensitivity of the present microarray embodiments varies according to the label used. For example, where radio-labeled or fluorescent-labeled dCTP is used, microarray sensitivity for any particular DNA target molecule will reflect the combined direct signals of all labeled cytosine residues incorporated therein.

Alternatively, dCTP comprising amplifiable labels is used to amplify labeling of genomic methylated cytosine residues. For example, the Tyramide Signal Amplification ("TSA™," from NEN Life Science Products, Inc.) system featuring Cyanine 3 Tyramide and Cyanine 5 Tyramide for signal generation, amplification and detection can be used (see e.g., Karsten et al. *N. A. R.*, Vol 30, No. 4 e4). TSA labeling and array hybridization are performed essentially as described in the instruction manuals for TSA™ labeling and detection using microarrays ("MICROMAX™ Human cDNA Micorarray system," NEN™ Life Science Products, Inc.; or "TSA™ Labeling and Detection Kit," PerkinElmer Life Sciences, Boston, Mass.) with minor modifications for BER reaction conditions (as described above).

Specifically, genomic DNA, for such embodiments, is digested according to the present invention with one or more restriction enzymes and treated with 5-methylcytosine deglycosylase (e.g., as in FIGS. 1, 2 or 3) to provide abasic DNA lacking cytosine at positions corresponding to methylated cytosine.

BER enzymes are used to specifically incorporate Biotin- or Fluorescein-labeled dCTP (e.g., using Biotin-11-dCTP (NEL 538A), or Fluorescein-12-dCTP (NEL424A)) into the resulting abasic DNA (e.g., by using Biotin-or Fluorescein-labeled dCTP for the cytosine-labeled dCTP of FIGS. 1, 2 or 3). Preferably, the BER repair is performed under the following conditions: 1× Buffer A (50 mM Tris-Cl (pH 8.8), 10 mM $MgCl_2$, 100 mM KCl, 1.0 mM DTT, 10% glycerol); 50 µM [$^{32}$P]-dCTP (or the functional equivalent of a non-radio label), 50 µM dGTP, 50 µM dTTP, 50 µM dATP; and 10 µg of restricted 5-methylcytosine deglycosylase-treated genomic DNA in a reaction volume of about 50 µl. Preferably, the BER reaction is for about 15 min at 37° C. The ratio of labeled- to unlabeled-dCTP is optimized to maximize label incorporation and thereby detection.

The Biotin- or Fluorescein-labeled DNA fragments are hybridized to the microarrays (typically overnight). The microarrays are washed and, in the case of Fluorescein-labeled DNA, incubated with anti-Fluorescein-horseradish peroxidase (anti-F1-HRP), which catalyzes the deposition of Cyanine 3-labeled tyramide amplification reagent. The enzymatic reaction results in deposition of numerous Cyanine 3 labels immediately adjacent to the immobilized HRP, and thus greatly amplifies the amount of tyramide relative to cDNA hapten. In the case of Biotin-labeled DNA, the washed microarrays are incubated with streptavidin-HRP, which binds to the hybridized Biotin-labeled DNA. The HRP component of the enzyme conjugate catalyzes the deposition of Cyanine 5 tyranamide.

Fluorescence detection is accomplished using, for example, a Genetic Microsystems 418 microarray scanner. Preferably, fluorescence detection is accomplished using a slide-scanning instrument containing two tuned lasers that excite both Cyanine 5 and Cyanine 3 dyes at the appropriate wavelengths. Preferably, laser detection of Cyanine 3 and Cyanine 5 fluorescence is performed using a confocal scanning instrument containing two tuned lasers that excite Cyanine dyes at the appropriate wavelengths. Preferably, image analysis is accomplished using art-recognized software designed for this purpose. Preferably, image processing and data extraction is performed using IMAGENE™ 4.1, powered by MATLAB™ (Biodiscovery, Inc., Santa Monica, Calif.;). Preferably, GENESPRING™ 3.1 is used to analyze quantified intensities.

Preferably, when comparisons are made between or among genomic DNA samples, reference genomic DNA is specifically labeled with Fluorescein, whereas each test genomic DNA is specifically labeled with Biotin (or the reference sample is labeled with Biotin, and each test sample with Fluorescein). Fluorescein- and Biotin-labeled genomic reference and test sample pairs are combined and simultaneously hybridized to the microarrays. For each such pair, the hybridized microarrays are washed and sequentially developed with anti-F1-HRP (plus Cyanine 3 tyranamide) followed by HRP inactivation, and then streptavidin-HRP (plus Cyanine 5 tyranamide). Fluorescence detection takes place as described above, to obtain a Cyanine 5:Cyanine 3 signal ratio reflecting the relative differences between the samples under analysis. Accuracy is enhanced by optionally using duplicate spots for each sequence on a microarray. Additionally, hybridizations are optionally repeated with the fluorophores reversed (i.e., reverse labeling of reference and test samples with biotin and fluorescein). Moreover, results are optionally confirmed using a variety of prior art methylation assay methods (summarized herein above, under "Background").

Figure 4:
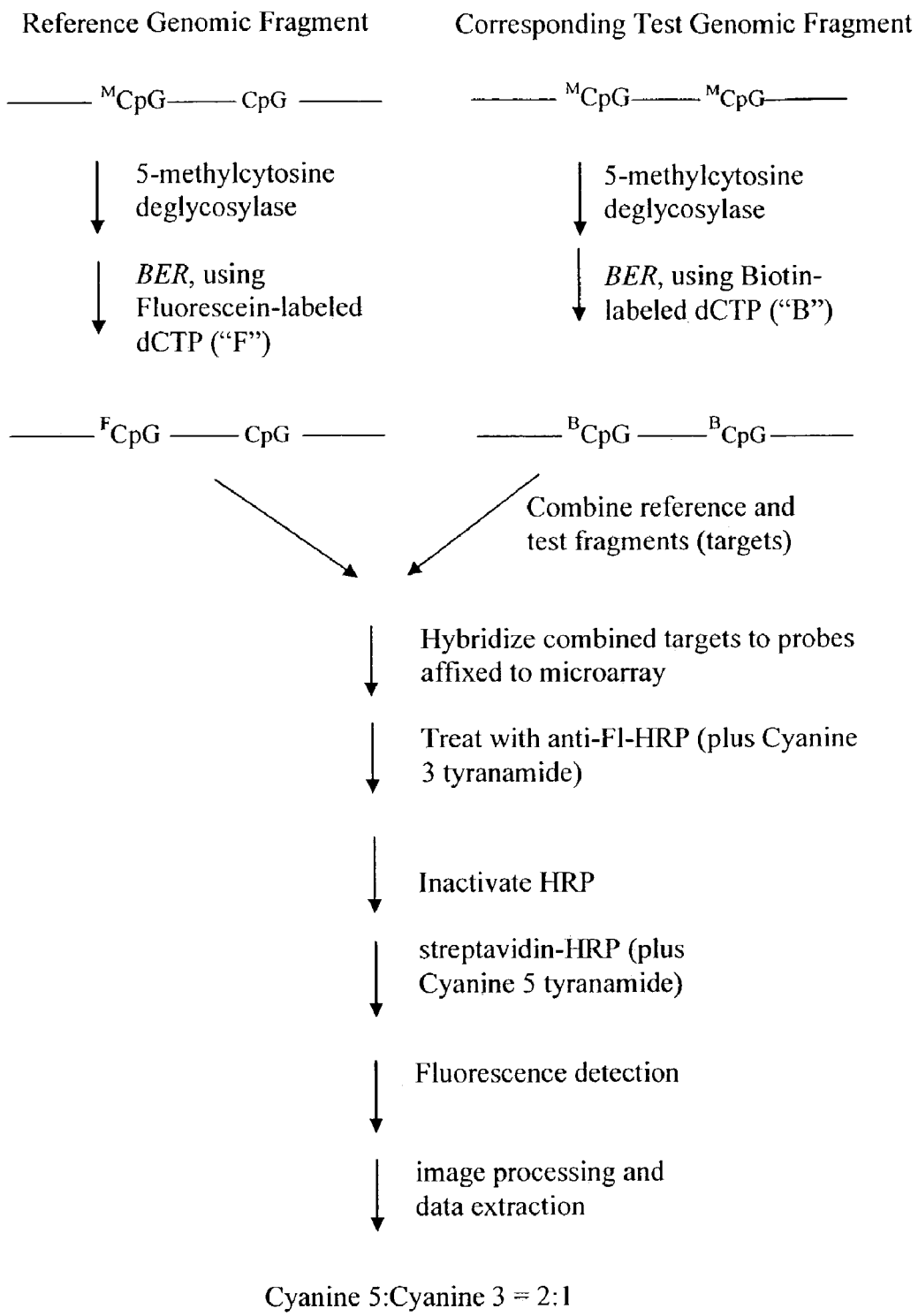
FIG. 4 illustrates a a high-throughput microarray TSA™ comparative embodiment according to the present invention. For simplicity, only a single reference and corresponding test genomic fragment is shown. The reference genomic DNA fragment is specifically labeled with Fluorescein at methylated cytosine positions using 5-MCDG and BER enzymes, whereas the corresponding test genomic DNA is specifically labeled with Biotin at methylated cytosine positions using 5-MCDG and BER enzymes. The combined fragments (targets) are simultaneously hybridized to a microarray (not shown) comprising affixed probe molecules. The washed microarray is sequentially developed with anti-Fl-HRP (plus Cyanine 3 tyranamide) followed by HRP inactivation, and then streptavidin-HRP (plus Cyanine 5 tyranamide). Fluorescence detection and image analysis is used to provide a Cyanine 5:Cyanine 3 signal ratio (here 2:1) for the particular complementary probe position on the microarray, indicating the relative degree of CpG methylation of the original corresponding genomic DNA fragments. Such microarray embodiments are useful for rapid identification of methylated CpG dinucleotide sequences in genomic DNA, or for high-throughput comparison of the status, extent or pattern of CpG methylation between or among reference and test samples.

FIG. 4 illustrates a high-throughput microarray TSA™ comparative embodiment according to the present invention. For simplicity, only a single reference and corresponding test genomic fragment is shown. The reference genomic DNA fragment is specifically labeled with Fluorescein, whereas the corresponding test genomic DNA is specifically labeled with Biotin. The Fluorescein- and Biotin-labeled genomic reference and test sample fragments (targets) are combined and simultaneously hybridized to microarray (not shown) probe molecules. The washed microarray is then sequentially developed with anti-F1-HRP (plus Cyanine 3 tyranamide) followed by HRP inactivation, and then streptavidin-HRP (plus Cyanine 5 tyranamide). Fluorescence detection and image analysis is used to provide a Cyanine 5:Cyanine 3 signal ratio (here 2:1) for the particular complementary probe position on the microarray, indicating the relative degree of CpG methylation of the original corresponding genomic DNA fragments.

Such microarray embodiments are useful for rapid identification of methylated CpG dinucleotide sequences in genomic DNA, or for high-throughput comparison of the status, extent or pattern of CpG methylation between or among reference and test samples.

Selective Isolation of Genomic DNA Fragments Comprising Methylated CpG Sequences Particular preferred embodiments of the present invention provide methods for the identification and selective isolation DNA fragments corresponding to methylated CpG-containing genomic DNA fragments.

A sample of isolated genomic DNA is digested with one or more restriction endonucleases as described herein above to produce restricted genomic DNA fragments. The restricted genomic DNA fragments are treated with 5-methylcytosine deglycosylase, and base excision repair (BER) enzymes in the presence of cytosine-labeled dCTP (all as described in detail herein above) to produce labeled genomic DNA fragments, whereby the 5-methylcytosine bases are removed and replaced by labeled cytosine in the repaired genomic DNA fragments.

The cytosine-labeled DNA fragments are directly isolated, based on the presence of the label. For example, where either biotin- or Fluorescein-dCTP is used to label the genomic DNA fragments, immobilized (e.g., on derivatized beads) Streptavidin or anti-fluorescein antibodies, respectively, are used to directly bind and isolate the biotin-labeled or fluorescein-labeled DNA fragments. The isolated labeled DNA fragments are subsequently separated (e.g., by proteolysis) from the immobilized Streptavidin or anti-fluorescein antibodies and, for identification, are either cloned, or amplified and cloned using art-recognized methods.

Thus, the present invention allows for the selective separation (from fragments lacking one or more CpG sequences) and direct isolation of all methylated CpG-containing genomic DNA fragments. The inventive selective isolation is afforded by the high specificity and affinity of the label-specific binding interactions. No other prior art method provides for such selective separation and direct isolation of all methylated CpG-containing genomic DNA fragments.

As will be obvious to those skilled in the art, genomic DNA fragments so isolated and cloned, allow for the construction of microarrays representing the entire genomic complement of methylated CpG sequences.

Additionally, in combination with the prior use of DNA methyltransferase, as in the above-described hypermethylation embodiments, these methods allow for the construction of microarrays representing the entire genomic complement of potentially methylatable CpG sequences.

| SEQUENCE ID NUMBERS | |
|---|---|
| Sequence | Accession number |
| SEQ ID NO:1 | AF 072250.1 |
| SEQ ID NO:2 | AA C68879.1 |
| SEQ ID NO:3 | AF 257107.1 |
| SEQ ID NO:4 | AA F68981.1 |
| SEQ ID NO:5 | U51166.1 |
| SEQ ID NO:6 | AA C50540.1 |
| SEQ ID NO:7 | AF 202114.1 |
| SEQ ID NO:8 | AA F14308.1 |
| SEQ ID NO:9 | variant: same as U51166.1, except T at position 670 instead of C. |
| SEQ ID NO:10 | variant: same as AA C50540.1, except S at aa 91 instead of P. |
| SEQ ID NO:11 | functional N-terminal deletion mutant ΔN273 of accession no. AA C68879.1 (Zhu et al., Nuc. Acids Res. 28:4157-4165, 2000) |
| SEQ ID NO:12 | functional N-terminal deletion mutant ΔN378 of accession no. AA C68879.1 (Zhu et al., Nuc. Acids Res. 28:4157-4165, 2000) |
| SEQ ID NO:13 | functional N-terminal deletion mutant ΔN433 of accession no. AA C68879.1 (Zhu et al., Nuc. Acids Res. 28:4157-4165, 2000) |

We claim:

1. A method for labeling CpG sequences corresponding to methylated CpG sequences in an isolated genomic DNA sample, comprising:
    (a) obtaining a sample of isolated genomic DNA;
    (b) digesting the isolated genomic DNA with a restriction endonuclease to produce genomic DNA fragments;
    (c) treating the genomic DNA fragments with a 5-methylcytosine deglycosylase, whereby one or more 5-methylcytosine bases are removed to produce abasic genomic DNA fragments; and
    (d) treating the abasic genomic DNA fragments with base excision repair (BER) enzymes in the presence of labeled dCTP, whereby 5-methylcytosine bases removed from the genomic DNA fragments by 5-methylcytosine deglycosylase are replaced by labeled cytosine in the one or more corresponding positions of the abasic genomic DNA fragments to produce labeled genomic DNA fragments, whereby specific labeling of CpG sequences corresponding to methylated CpG sequences is achieved.

2. The method of claim 1, further comprising digesting the labeled genomic DNA fragments with one or more restriction endonucleases.

3. The method of claim 1, further comprising: resolving, at least in part, the labeled genomic DNA fragments; detecting the resolved fragments based on the presence of the label; and determining the status, extent, or pattern of CpG methylation for one or more CpG sequences of the resolved fragments.

4. The method of claim 3, wherein resolving, at least in part, the labeled genomic DNA fragments, detecting the resolved fragments based on the presence of the label, and determining the status, extent, or pattern of CpG methylation for one or more CpG sequences of the resolved fragments is accomplished by using a method selected from the group consisting of restriction landmark genomic scanning (RLGS) methods, virtual genome scanning (VGS) methods, and microarray hybridization methods.

5. The method of claim 1, wherein the BER enzymes are selected from the group consisting of short-patch BER enzymes, long-patch BER enzymes, purified or partially-purified BER enzymes, recombinant BER enzymes, and combinations thereof.

6. The method of claim 5, wherein the BER enzymes are selected from the group consisting of mammalian BER enzymes, avian BER enzymes, yeast BER enzymes, prokaryotic BER enzymes, and combinations thereof.

7. The method of claim 6, wherein the BER enzymes are selected from the group consisting of human BER enzymes, chicken BER enzymes, mouse BER enzymes, yeast BER enzymes, bacterial BER enzymes, and combinations thereof.

8. The method of claim 1, wherein the 5-methylcytosine deglycosylase is specific for methylated CpG dinucleotide sequences, or can be so-rendered.

9. The method of claim 1, wherein the 5-methylcytosine deglycosylase is specific specific for fully-methylated CpG dinucleotide sequences, or can be so-rendered.

10. The method of claim 1, wherein the 5-methylcytosine deglycosylase is of human or avian origin, or recombinant versions thereof.

11. The method of claim 1, wherein the 5-methylcytosine deglycosylase is selected from the group consisting of SEQ ID NOs:2, 4, 6, 8, 10-12, and 13.

12. The method of claim 1, wherein the dCTP label is selected from the group consisting of radiolabels, fluorescent labels, phosphorescent labels, enzymic labels, mass labels detectable in a mass spectrometer, amplifiable labels, and combinations thereof.

13. The method of claim 12, wherein the amplifiable label is biotin- or fluorescein-labeled dCTP.

14. The method of claim 1, wherein treating the genomic DNA fragments with 5-methylcytosine deglycosylase occurs simultaneously with base excision repair (BER) in the presence of labeled dCTP.

15. The method of claim 1, further comprising, in the case of staggered ends resulting from restriction endonuclease digestion, repairing said staggered ends by filling-in or blunting.

16. A method for comparing CpG methylation status, extent or pattern between or among reference and test genomic DNA samples, comprising:
    (a) obtaining a reference and a test sample of isolated genomic DNA;
    (b) digesting the respective isolated genomic DNA samples with one or more restriction endonucleases to produce genomic DNA fragments;
    (c) treating the respective genomic DNA fragments with a 5-methylcytosine deglycosylase, whereby one or more 5-methylcytosine bases are removed to produce abasic genomic DNA fragments;
    (d) treating the respective abasic genomic DNA fragments with base excision repair (BER) enzymes in the presence of labeled dCTP, whereby 5-methylcytosine bases removed from the genomic DNA fragments by 5-methylcytosine deglycosylase are replaced by labeled cytosine in the one or more corresponding positions of the abasic genomic DNA fragments to produce labeled genomic DNA fragments;

(e) resolving, at least in part, the respective labeled genomic DNA fragments; and (f) detecting the respective methylated nucleic acid fragments based on the presence of the label, whereby a comparison of status, extent, or pattern of CpG methylation is enabled.

17. The method of claim 16, further comprising digestion of the respective labeled genomic DNA fragments with one or more restriction endonucleases.

18. The method of claim 16, wherein the BER enzymes are selected from the group consisting of short-patch BER enzymes, long-patch BER enzymes, purified or partially-purified BER enzymes, recombinant BER enzymes, and combinations thereof.

19. The method of claim 18, wherein the BER enzymes are selected from the group consisting of mammalian BER enzymes, avian BER enzymes, yeast BER enzymes, prokaryotic BER enzymes, and combinations thereof.

20. The method of claim 19, wherein the BER enzymes are selected from the group consisting of human BER enzymes, chicken BER enzymes, mouse BER enzymes, yeast BER enzymes, bacterial BER enzymes, and combinations thereof.

21. The method of claim 16, wherein the 5-methylcytosine deglycosylase is specific for methylated CpG dinucleotide sequences, or can be so-rendered.

22. The method of claim 16, wherein the 5-methylcytosine deglycosylase is specific for fully-methylated CpG dinucleotide sequences, or can be so-rendered.

23. The method of claim 16, wherein the 5-methylcytosine deglycosylase is of human or avian origin, or recombinant versions thereof.

24. The method of claim 16, wherein the 5-methylcytosine deglycosylase is selected from the group consisting of SEQ ID NOs:2, 4, 6, 8, 10-12, and 13.

25. The method of claim 16, wherein the dCTP label is selected from the group consisting of radiolabels, fluorescent labels, phosphorescent labels, enzymic labels, mass labels detectable in a mass spectrometer, amplifiable labels, and combinations thereof.

26. The method of claim 25, wherein the amplifiable label is biotin- or fluorescein-labeled dCTP.

27. The method of claim 16, wherein treating the genomic DNA fragments with 5-methylcytosine deglycosylase occurs simultaneously with base excision repair (BER) in the presence of labeled dCTP.

28. The method of claim 16, further comprising, in the case of staggered ends resulting from restriction endonuclease digestion, repairing said staggered ends by filling-in or blunting.

29. A method for selective isolation of genomic DNA fragments corresponding to methylated CpG-containing genomic DNA fragments, comprising:

(a) obtaining a sample of isolated genomic DNA;

(b) digesting the isolated genomic DNA sample with one or more restriction endonucleases to produce genomic DNA fragments;

(c) treating the genomic DNA fragments with a 5-methylcytosine deglycosylase to remove one or more 5-methylcytosine bases to produce abasic genomic DNA fragments;

(d) treating the abasic genomic DNA fragments with base excision repair (BER) enzymes in the presence of labeled dCTP, whereby 5-methylcytosine bases removed from the genomic DNA fragments by 5-methylcytosine deglycosylase are replaced by labeled cytosine in the one or more corresponding positions of the abasic genomic DNA fragments to produce labeled genomic DNA fragments; and (e) isolating the labeled DNA fragments based on the presence of the label, whereby labeled DNA fragments are separated, at least in part, from non-labeled DNA fragments.

30. The method of claim 29, wherein the labeled dCTP used to label the genomic DNA fragments is at least one of biotin- or Fluorescein-dCTP.

31. The method of claim 29, wherein isolating the labeled DNA fragments based on the presence of the label is accomplished by label-specific binding interactions.

32. The method of claim 31, wherein the label used to label the genomic DNA fragments is at least one of biotin- or Fluorescein-dCTP, and correspondingly wherein at least one of Streptavidin or anti-fluorescein antibodies are used to specifically bind to the biotin-labeled or fluorescein-labeled DNA fragments, respectively.

33. The method of claim 32, wherein treating the isolated genomic DNA with 5-methylcytosine deglycosylase occurs simultaneously with base excision repair (BER) in the presence of labeled dCTP.

34. A method for labeling potentially-methylatable CpG sequences in CpG-containing genomic DNA fragments, comprising:

(a) obtaining a sample of isolated genomic DNA;

(b) digesting the isolated genomic DNA sample with one or more restriction endonucleases to produce genomic DNA fragments;

(c) treating the genomic DNA fragments with a DNA methyltransferase in the presence of a methyl donor to produce hypermethylated genomic DNA fragments;

(d) treating the hypermethylated genomic DNA fragments with a 5-methylcytosine deglycosylase to remove one or more hypermethylated 5-methylcytosine bases to produce abasic genomic DNA fragments;

(e) treating the abasic genomic DNA fragments with base excision repair (BER) enzymes in the presence of labeled dCTP, whereby 5-methylcytosine bases removed from the genomic DNA fragments by 5-methylcytosine deglycosylase are replaced by labeled cytosine in the one or more corresponding positions of the abasic genomic DNA fragments to produce labeled genomic DNA fragments.

35. The method of claim 34, further comprising digesting the labeled genomic DNA fragments with one or more restriction endonucleases.

36. The method of claim 34, further comprising: resolving, at least in part, the labeled genomic DNA fragments; detecting the resolved fragments based on the presence of the label; and determining the status, extent, or pattern of CpG methylation for one or more CpG sequences of the resolved fragments.

37. The method of claim 36, wherein resolving, at least in part, the labeled genomic DNA fragments, detecting the resolved fragments based on the presence of the label, and determining the status, extent, or pattern of CpG methylation for one or more CpG sequences of the resolved fragments is accomplished by using a method selected from the group consisting of restriction landmark genomic scanning (RLGS) methods, virtual genome scanning (VGS) methods, and microarray hybridization methods.

38. The method of claim 34, wherein the BER enzymes are selected from the group consisting of short-patch BER enzymes, long-patch BER enzymes, purified or partially-purified BER enzymes, recombinant BER enzymes, and combinations thereof.

39. The method of claim 38, wherein the BER enzymes are selected from the group consisting of mammalian BER enzymes, avian BER enzymes, yeast BER enzymes, prokaryotic BER enzymes, and combinations thereof.

40. The method of claim 39, wherein the BER enzymes are selected from the group consisting of human BER enzymes, chicken BER enzymes, mouse BER enzymes, yeast BER enzymes, bacterial BER enzymes, and combinations thereof.

41. The method of claim 34, wherein the 5-methylcytosine deglycosylase is specific for methylated CpG dinucleotide sequences, or can be so-rendered.

42. The method of claim 34, wherein the 5-methylcytosine deglycosylase is specific for fully-methylated CpG dinucleotide sequences, or can be so-rendered.

43. The method of claim 34, wherein the 5-methylcytosine deglycosylase is of human or avian origin, or recombinant versions thereof.

44. The method of claim 34, wherein the 5-methylcytosine deglycosylase is selected from the group consisting of SEQ ID NOs:2, 4, 6, 8, 10-12, and 13.

45. The method of claim 34, wherein the dCTP label is selected from the group consisting of radiolabels, fluorescent labels, phosphorescent labels, enzymic labels, mass labels detectable in a mass spectrometer, amplifiable labels, and combinations thereof.

46. The method of claim 45, wherein the amplifiable label is biotin- or fluorescein-labeled dCTP.

47. The method of claim 34, wherein treating the genomic DNA fragments with 5-methylcytosine deglycosylase occurs simultaneously with base excision repair (BER) in the presence of labeled dCTP.

48. The method of claim 34, further comprising, in the case of staggered ends resulting from restriction endonuclease digestion, repairing said staggered ends by filling-in or blunting.

49. A method for differentially labeling existing $^{M}$CpG Sequences, and potentially-methylatable CpG sequences in CpG-containing genomic DNA fragments, comprising:
(a) obtaining a sample of isolated genomic DNA;
(b) digesting the isolated genomic DNA sample with one or more restriction endonucleases to produce genomic DNA fragments;
(c) treating the genomic DNA fragments with a 5-methylcytosine deglycosylase to remove one or more 5-methylcytosine bases to produce abasic genomic DNA fragments;
(d) treating the abasic genomic DNA fragments with base excision repair (BER) enzymes in the presence of dCTP labeled with a first label, whereby 5-methylcytosine bases removed from the genomic DNA fragments by 5-methylcytosine deglycosylase are replaced by labeled cytosine in the one or more corresponding positions of the abasic genomic DNA fragments to produce labeled genomic DNA fragments, and wherein the first label precludes transfer by DNA methyltransferases of a methyl group from S-adenosylmethionine to the 5'-position of the labeled cytosine;
(e) treating the labeled genomic DNA fragments with a DNA methyltransferase in the presence of a methyl donor to produce hypermethylated labeled genomic DNA fragments;
(f) treating the hypermethylated labeled genomic DNA fragments with 5-methylcytosine deglycosylase to remove one or more hypermethylated 5-methylcytosine bases to produce abasic labeled genomic DNA fragments; and
(g) treating the abasic labeled genomic DNA fragments with base excision repair (BER) enzymes in the presence of dCTP labeled with a second label, whereby hypermethylated 5-methylcytosine bases removed from the hypermethylated labeled genomic DNA fragments by 5-methylcytosine deglycosylase are replaced by labeled cytosine in the one or more corresponding positions of the abasic labeled genomic DNA fragments to produce doubly-labeled genomic DNA fragments, and whereby the existing $^{M}$CpG sequences and the potentially-methylatable CpG sequences in the CpG-containing genomic DNA fragments are differentially labeled by the first and second labels, respectively, in the doubly-labeled genomic DNA fragments.

50. The method of claim 49, further comprising digesting the labeled, or doubly-labeled genomic DNA fragments with one or more restriction endonucleases.

51. The method of claim 49, further comprising: resolving, at least in part, the doubly-labeled genomic DNA fragments; detecting the resolved fragments based on the presence of at least one of the first or second labels; and correspondingly determining the status, extent, or pattern of the existing $^{M}$CpG sequences or of the potentially-methylatable CpG sequences, respectively, in the CpG-containing genomic DNA fragments, for one or more CpG sequences of the resolved fragments.

52. The method of claim 51, wherein resolving, at least in part, the doubly-labeled genomic DNA fragments, detecting the resolved fragments based on the presence of at least one of the first or second labels; and correspondingly determining the status, extent, or pattern of the existing $^{M}$CpG sequences or of the potentially-methylatable CpG sequences, respectively, is accomplished by using a method selected from the group consisting of restriction landmark genomic scanning (RLGS) methods, virtual genome scanning (VGS) methods, and microarray hybridization methods.

53. The method of claim 49, wherein the BER enzymes are selected from the group consisting of short-patch BER enzymes, long-patch BER enzymes, purified or partially-purified BER enzymes, recombinant BER enzymes, and combinations thereof.

54. The method of claim 49, wherein the first and second labels are individually selected from the group consisting of radiolabels, fluorescent labels, phosphorescent labels, enzymic labels, mass labels detectable in a mass spectrometer, amplifiable labels, and combinations thereof.

55. The method of claim 52, wherein the first label is Biotin, wherein the second label is Fluorescein, and wherein detecting the resolved fragments is accomplished by differentially detecting the first and second labels using a tyramide signal amplification protocol.

56. The method of claim 49, wherein treating the genomic DNA fragments, or the labeled genomic DNA fragments, or both with 5-methylcytosine deglycosylase occurs simultaneously with base excision repair (BER) in the presence of the labeled dCTP.

57. A method for specifically labeling cytosine bases in methylated CpG dinucleotides in genomic DNA sequences, comprising:
treating genomic DNA having one or more 5-methylcytosine bases with 5-methylcytosine deglycosylase to remove one or more 5-methylcytosine bases to provide genomic DNA having one or more abasic sites; and treating the genomic DNA having one or more abasic sites with excision repair (BER) enzymes in the presence of labeled dCTP, wherein 5-methylcytosine removed from the genomic DNA fragments by the 5-methylcytosine deglycosylase is replaced by labeled cytosine in the one or more abasic site positions.

58. The method of claim 57, further comprising digesting the labeled genomic DNA with one or more restriction endonucleases to provide labeled genomic DNA fragments.

59. The method of claim 58, further comprising: resolving, at least in part, the labeled genomic DNA fragments; detecting the resolved fragments based on the presence of the label; and determining the status, extent, or pattern of CpG methylation for one or more CpG sequences of the resolved fragments.

60. The method of claim 59, wherein resolving, at least in part, the labeled genomic DNA fragments, detecting the resolved fragments based on the presence of the label, and determining the status, extent, or pattern of CpG methylation for one or more CpG sequences of the resolved fragments is accomplished by using a method selected from the group consisting of restriction landmark genomic scanning (RLGS) methods, virtual genome scanning (VGS) methods, and microarray hybridization methods.

61. The method of claim 57, wherein the BER enzymes are selected from the group consisting of short-patch BER enzymes, long-patch BER enzymes, purified or partially-purified BER enzymes, recombinant BER enzymes and combinations thereof.

62. The method of claim 61, wherein the BER enzymes are selected from the group consisting of mammalian BER enzymes, avian BER enzymes, yeast BER enzymes, prokaryotic BER enzymes, and combinations thereof.

* * * * *